United States Patent
Yu et al.

(10) Patent No.: US 12,077,784 B2
(45) Date of Patent: Sep. 3, 2024

(54) SUSPENSION SYSTEM FOR ADENO ASSOCIATED VIRUS PRODUCTION

(71) Applicant: Life Technologies Corporation, Carlsbad, CA (US)

(72) Inventors: Xin Yu, Zhangiagang (CN); Xavier de Mollerat du Jeu, Encinitas, CA (US); Chao Yan Lin, Germantown, MD (US); Jian Liu, Carlsbad, CA (US); Jonathan Zmuda, Frederick, MD (US)

(73) Assignee: Life Technologies Corporation, Carlsbad, CA (US)

(*) Notice: Subject to any disclaimer, the term of this patent is extended or adjusted under 35 U.S.C. 154(b) by 39 days.

(21) Appl. No.: 18/168,396

(22) Filed: Feb. 13, 2023

(65) Prior Publication Data
US 2023/0193214 A1    Jun. 22, 2023

Related U.S. Application Data

(62) Division of application No. 16/798,193, filed on Feb. 21, 2020, now Pat. No. 11,608,491.

(60) Provisional application No. 62/809,407, filed on Feb. 22, 2019.

(51) Int. Cl.
| | | |
|---|---|---|
| C12N 1/06 | (2006.01) | |
| C12N 1/22 | (2006.01) | |
| C12N 7/00 | (2006.01) | |
| C12N 15/10 | (2006.01) | |
| C12N 15/86 | (2006.01) | |

(52) U.S. Cl.
CPC .............. *C12N 7/00* (2013.01); *C12N 1/06* (2013.01); *C12N 15/86* (2013.01); *C12N 2750/14041* (2013.01); *C12N 2750/14152* (2013.01)

(58) Field of Classification Search
CPC ........... C12N 2750/14152; C12N 1/06; C12N 15/86; C12Q 1/6809; C12Q 2522/101
See application file for complete search history.

(56) References Cited

U.S. PATENT DOCUMENTS

| | | |
|---|---|---|
| 6,413,776 B1 | 7/2002 | Vogels et al. |
| 2009/0069266 A1 | 3/2009 | Dean et al. |
| 2013/0316400 A1 | 11/2013 | Vasu et al. |
| 2015/0211021 A1 | 7/2015 | De Mollerat Du Jeu |
| 2017/0016043 A1 | 1/2017 | Zmuda et al. |
| 2018/0135077 A1 | 5/2018 | Yu et al. |
| 2018/0143117 A1 | 5/2018 | He |

FOREIGN PATENT DOCUMENTS

| | | |
|---|---|---|
| CN | 106456793 A | 2/2017 |
| CN | 108085301 A | 5/2018 |
| CN | 108779074 A | 11/2018 |
| WO | WO-2015031686 A1 | 3/2015 |
| WO | WO-2017112948 A1 | 6/2017 |
| WO | WO-2017201258 A1 | 11/2017 |
| WO | WO-2017214378 A1 | 12/2017 |
| WO | WO-2018226887 A1 | 12/2018 |

OTHER PUBLICATIONS

Cervera L., et al., "Selection and Optimization of Transfection Enhancer Additives for Increased Virus-Like Particle Production in HEK293 Suspension Cell Cultures," Applied Microbiology and Biotechnology, 2015, vol. 99, pp. 9935-9949.
Durocher et al., "Scalable Serum-Free Production of Recombinant Adeno-Associated Virus Type 2 by Transfection of 293 Suspension Cells", Journal of Virological Methods, vol. 144, No. 1-2, Jul. 27, 2007, pp. 32-40, XP022170236.
Grieger et al., "Production of Recombinant Adeno-associated Virus Vectors Using Suspension HEK293 Cells and Continuous Harvest of Vector From the Culture Media for GMP FIX and FLT1 Clinical Vector", Molecular Therapy: The Journal of the American Society of Gene Therapy, vol. 24, No. 2, Feb. 1, 2016, pp. 287-297, XP055436946.
PCT/US2020/019355, Search Report and Written Opinion, Apr. 23, 2020.

*Primary Examiner* — Barry A Chestnut

(57) ABSTRACT

The instant technology relates to a production system to produce AAV vectors in a serum free suspension platform and at high titers. This technology uses reagents comprising media, cells, transfection reagent, AAV enhancer, and a lysis buffer, each of which is designed to provide maximal AAV production from suspension culture of mammalian cells, e.g. HEK293 cells. With this new system we are able to deliver up to about $2 \times 10^{11}$ viral genomes per milliliter (vg/mL) of unconcentrated AAV vectors.

20 Claims, 12 Drawing Sheets

FIG. 12A
FIG. 12B
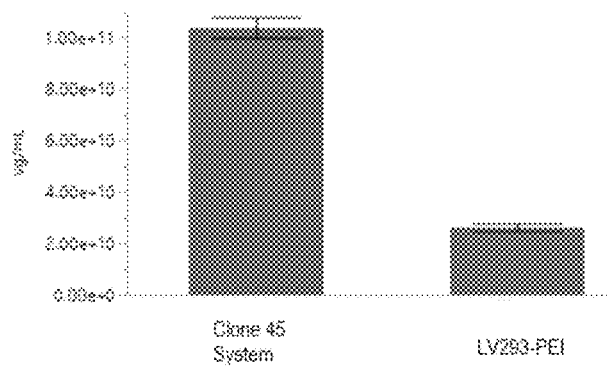
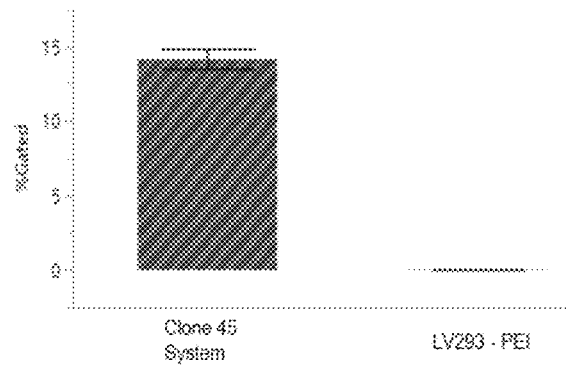
FIG. 13A
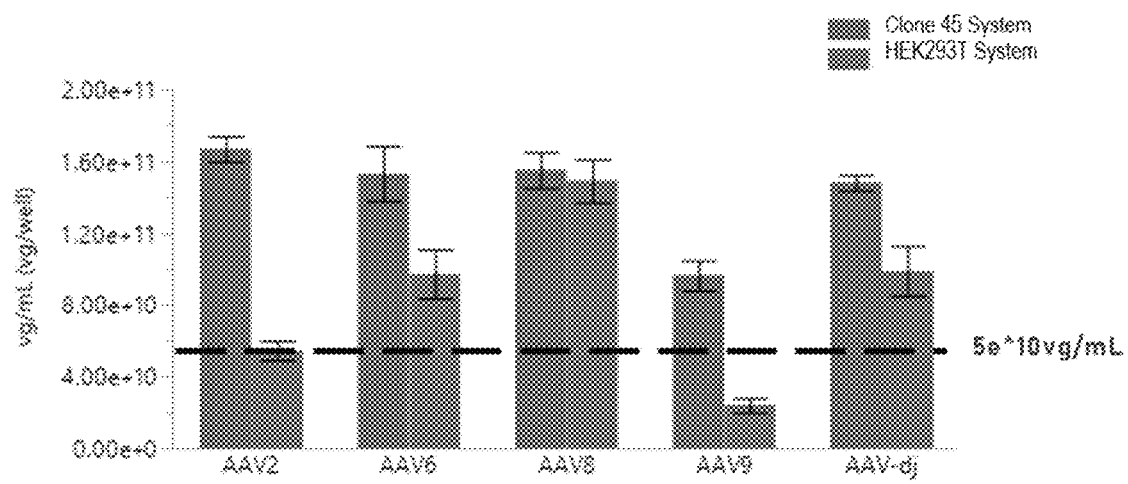

SUSPENSION SYSTEM FOR ADENO ASSOCIATED VIRUS PRODUCTION

CROSS-REFERENCE TO RELATED APPLICATIONS

This application is a divisional of U.S. patent application Ser. No. 16/798,193, filed Feb. 21, 2020, which claims the benefit of U.S. Provisional Application No. 62/809,407 filed Feb. 22, 2019, which applications are herein incorporated by reference in their entirety.

BACKGROUND

Adeno-associated virus (AAV) is a small DNA virus that infects human and some non-human primate cells. AAV is not known to cause disease and has low immunogenicity in humans. AAV vectors can be produced that contain DNA sequences of interest, with few or no viral genes. These advantages have led to the use of AAV vectors in gene therapy and other clinical and research purposes.

Large-scale methods of producing AAV vectors and producing high titers is needed.

SUMMARY OF THE INVENTION

The instant technology generally relates to a new AAV system to produce vectors in a serum free suspension platform and at high titers. This technology employs a newly developed propriety set of good manufacturing process (GMP) reagents comprising media, cells, transfection reagent, AAV enhancer, and a lysis buffer, each of which is designed to provide maximal AAV production from suspension culture of mammalian cells. With this new system we are able to deliver up to about $2 \times 10^{11}$ viral genomes per milliliter (vg/mL) of unconcentrated AAV vectors (that is, vectors that have not been further concentrated after harvest using the harvesting methods described herein).

In one aspect, herein is provided a method for AAV vector production, including: (i) culturing mammalian cells; (ii) transfecting the mammalian cells with an AAV transfer vector using a transfection reagent; (iii) contacting transfected cells with an AAV enhancer; (iv) and culturing the transfected cells in suspension culture for a period of time sufficient for packaging of the AAV vector, thereby producing a transfected AAV cell culture. In embodiments, the mammalian cells are cultured in suspension culture. In embodiments, the method includes harvesting AAV from the transfected AAV cell culture. In embodiments, the AAV are harvested using a lysis buffer. In embodiments, the transfection step includes contacting the cells with a transfection booster.

In embodiments, the method includes titering the harvested AAV. In embodiments, the AAV is titered using quantitative PCR. In embodiments, the harvested AAV has a titer of at least about $2 \times 10^{10}$ viral genomes per milliliter (vg/mL). In embodiments, the harvested AAV has a titer between about $2 \times 10^{10}$ vg/mL and about $2 \times 10^{11}$ vg/mL.

In embodiments, the cells are cultured in a volume of about 10 milliliters (mL) to about 800 liters (L). In embodiments, the cells are cultured in a volume of about 1 L to about 10 L. In embodiments, the cells are transfected in a volume of about 15 milliliters (mL) to about 200 liters (L). In embodiments, the cells are transfected in a volume of about 1 L to about 2 L.

In embodiments, the cells are cultured in a bioreactor.

In embodiments, the cells are cultured in a media that supports growth and expansion of HEK293 cells. In embodiments, the cells are contacted with an AAV production enhancer during culture (e.g., after transfection).

In one aspect, herein is provided an AAV production system, including HEK293 cells, an AAV transfer vector, a packaging plasmid, an AAV production enhancer, and cell culture media that supports growth and expansion of the HEK293 cells. In embodiments, the AAV production system includes a transfection reagent. In embodiments, the AAV production system includes a transfection booster. In embodiments, the AAV production system includes a lysis buffer. In embodiments, the HEK293 cells are present at a density of at least about $0.3 \times 10^6$ cells/mL. In embodiments, the HEK293 cells are present at a density of at least about $2 \times 10^6$ cells/mL. In embodiments, the HEK293 cells are present at a density of between about $0.3 \times 10^6$ cells/mL and about $1 \times 10^7$ cells/mL. In an embodiment, the AAV vector is present at a titer of at least about $2 \times 10^{10}$ viral genomes per milliliter (vg/mL) after harvesting.

In embodiments, the lysis buffer includes a surfactant. In embodiments, the surfactant is Triton-100, Triton-alter, NP-40, poloxamer 188, or NDSB-201. In embodiments, the lysis buffer does not include a surfactant. In embodiments, the lysis buffer comprises at least one of: Tris-HCl, tricine HCL, sodium citrate, sodium chloride, citric acid, EDTA, tri-potassium EDTA, sodium hydroxide, and sodium dihydrogen phosphate. In embodiments, the lysis buffer comprises at least one detergent. In embodiments, the detergent is CHAP, CHAPS, CHAPSO, big CHAP, octylthioglucoside, and/or sodium deoxycholate.

In embodiments, the AAV production enhancer includes one or more of a histone deacetylase (HDAC) inhibitor, sodium proprionate, egg lecithin, lithium acetate, trichostatin hydroxyurea, nocodazole-DMSO, NaCl, and caffeine. In embodiments, the HDAC inhibitor is apicidin, belinostat, CI-994, CRA-024781, curcumin, panobinostat, sodium butyrate, sodium phenylbutyrate, suberoylanilide hydroxamic acid, trichostatin A, and/or valproic acid. In embodiments, the HDAC inhibitor is sodium butyrate, sodium phenylbutyrate, trichostatin A, and/or valproic acid. In embodiments, the AAV enhancer is added between about 0 hour and about 6 hours after transfection.

In embodiments, the transfection reagent includes a cationic lipid. In embodiments, the transfection reagent further includes a peptide. In embodiments, the transfection booster includes a cationic lipid. In embodiments, the transfection booster includes a peptide. In embodiments, the peptide is a membrane-penetrating peptide. Non-limiting examples of membrane-penetrating peptides are provided in U.S. Pat. No. 9,856,496, which is incorporated herein by reference in its entirety. In embodiments, the transfection booster is used at a ratio of between 5:1 and about 1:5 (volume/weight) transfection booster:DNA.

In embodiments, the mammalian cells are HEK293 cells or a derivative of HEK293 cells. In embodiments, the HEK293 cells have been adapted for high AAV expression in the AAV vector production system. In embodiments, the HEK293 cells can grow in suspension culture at a density of at least $0.3 \times 10^6$ cells per milliliter (cells/mL). In embodiments, the HEK293 cells can grow in suspension culture at a density of up to $1.2 \times 10^7$ cells per milliliter (cells/mL). In embodiments, the cells are transfected at a cell density between about 2.5×10$^6$ and about 4×10$^6$ cells/mL.

In embodiments, a helper virus is not used. In embodiments, the method includes transfecting the cells with packaging plasmids. In embodiments, the AAV production system includes packaging plasmids. In embodiments, the packaging plasmids comprise pRC and pHelper.

In embodiments, the cells are not centrifuged prior to harvesting AAV.

In embodiments, the cells do not comprise large T antigen.

In an aspect, provided herein is a kit for adeno-associated virus (AAV) production. In embodiments, the kit includes HEK293 cells; an enhancer; a transfection reagent comprising a cationic lipid; and a cell culture media that supports growth and expansion of the HEK293 cells. In embodiments, the transfection reagent contains a cationic lipid and a peptide.

In embodiments, the kit also includes a transfection booster. In embodiments, the transfection booster contains a peptide.

In embodiments, the kit also includes a lysis buffer. In embodiments, the lysis buffer contains at least one surfactant. In embodiments, the surfactant is Triton-100, Triton-alter, NP-40, poloxamer 188, and/or NDSB-201. In embodiments, the lysis buffer contains Tris-HCl, sodium citrate, Tricine HCL, sodium chloride, citric acid, EDTA, tri-potassium EDTA, sodium hydroxide, and/or sodium dihydrogen phosphate. In embodiments, the lysis buffer includes at least one detergent. In embodiments, the detergent is CHAP, CHAPS, CHAPSO, big CHAP, deoxy Big CHAP, Triton X-114, octylthioglucoside, and/or sodium deoxycholate.

BRIEF DESCRIPTION OF THE DRAWINGS

FIG. 11A compares viral titers (vg/mL) obtained for different AAV serotypes; FIG. 11B compares infectivity (as % GFP in Ht1080) of the harvested AAV2 and AAV6 from each clonal cell line.

FIGS. 12A-12B show a comparison of the clone 45 AAV system and an LV293-PEI system in AAV6 production (vg/ml, FIG. 12A) and AAV6 infectivity (as % GFP in Ht1080, FIG. 12B) following harvest.

FIGS. 13A-13B show a comparison of the clone 45 AAV system and an HEK293T-PEI system in AAV production: FIG. 13A compares viral titers (vg/mL) obtained for different AAV serotypes; FIG. 13B compares infectivity (as % GFP in Ht1080) of the harvested AAV2, AAV6 and AAV-dj from each system.

DETAILED DESCRIPTION

Figure 1:
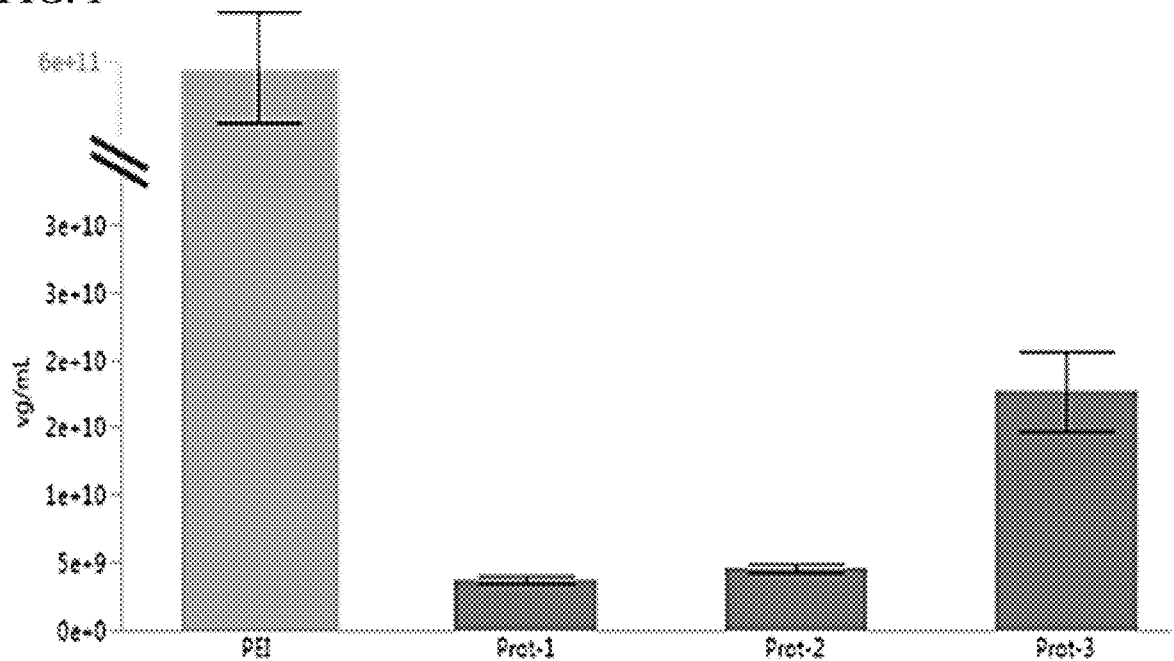
FIG. 1 shows the effect of different conditions on the production of AAV2. AAV2 virus were produced by adherent HEK293 cells (6-well plate) transfected by polyethylenimine (PEI) compared to System 1 under three different conditions: Prot-1 (enhancer 1 and supplement 1), Prot-2 (supplement 1, no enhancer), Prot-3 (enhancer 1, no supplement).

After reading this description it will become apparent to one skilled in the art how to implement the invention in various alternative embodiments and alternative applications. However, all the various embodiments of the present invention will not be described herein. It will be understood that the embodiments presented here are presented by way of an example only, and not limitation. As such, this detailed description of various alternative embodiments should not be construed to limit the scope or breadth of the present invention as set forth below.

Before the present invention is disclosed and described, it is to be understood that the aspects described below are not limited to specific compositions, methods of preparing such compositions, or uses thereof as such may, of course, vary. It is also to be understood that the terminology used herein is for the purpose of describing particular aspects only and is not intended to be limiting.

The detailed description of the invention is divided into various sections only for the reader's convenience and disclosure found in any section may be combined with that in another section. Titles or subtitles may be used in the specification for the convenience of a reader, which are not intended to influence the scope of the present invention.

Definitions

Unless defined otherwise, all technical and scientific terms used herein have the same meaning as commonly understood by one of ordinary skill in the art to which this invention belongs. In this specification and in the claims that follow, reference will be made to a number of terms that shall be defined to have the following meanings:

The terminology used herein is for the purpose of describing particular embodiments only and is not intended to be limiting of the invention. As used herein, the singular forms "a", "an" and "the" are intended to include the plural forms as well, unless the context clearly indicates otherwise.

"Optional" or "optionally" means that the subsequently described event or circumstance can or cannot occur, and that the description includes instances where the event or circumstance occurs and instances where it does not.

The term "about" when used before a numerical designation, e.g., temperature, time, amount, concentration, and such other, including a range, indicates approximations which may vary by (+) or (−) 10%, 5%, 1%, or any subrange or subvalue there between. Preferably, the term "about" when used with regard to a dose amount means that the dose may vary by +/−10%.

"Comprising" or "comprises" is intended to mean that the compositions and methods include the recited elements, but not excluding others. "Consisting essentially of" when used to define compositions and methods, shall mean excluding other elements of any essential significance to the combination for the stated purpose. Thus, a composition consisting essentially of the elements as defined herein would not exclude other materials or steps that do not materially affect the basic and novel characteristic(s) of the claimed invention. "Consisting of" shall mean excluding more than trace elements of other ingredients and substantial method steps. Embodiments defined by each of these transition terms are within the scope of this invention.

Adeno Associated Virus (AAV) Production System

The term "cell" as used herein refers includes all types of eukaryotic and prokaryotic cells. In some embodiments, the term refers to eukaryotic cells, especially mammalian cells. In certain exemplary though non-limiting embodiments, the term "cell" is meant to refer to human embryonic kidney (HEK) or human 293 cells, or a variant thereof, such as, e.g., a 293 (HEK293) variant that can grow in suspension. In some embodiments, variants of 293 cells that can grow, proliferate and be transfected in suspension culture, in particular those variants that can be cultured at high density (e.g., at least about $2\times10^6$ cells/mL, at least about $3\times10^6$ cells/mL, or even optionally at least about $4\times10^6$ cells/mL or about $1.2\times10^6$ cells/mL).

In some embodiments, the term "high density" when used in the context of culturing cells and conducting transfection workflows, generally refers to a known cell line, or a variant of a known cell line, that can be grown or cultured in an appropriate cell culture medium to densities of at least about $2\times10^6$ cells/mL, at least about $3\times10^6$ cells/mL, or even optionally at least about $4\times10^6$ cells/mL, while still retaining the ability to be transfected at high efficiency and are able to express a target AAV vector at high titer, for example $5\times10^{10}$ viral genomes per mL (vg/mL) or more.

In some embodiments, the cells are adapted for high density cell culture. This refers to a cell lineage or a (non-clonal) population of cells derived from the same parental cell lineage that has been adapted to grow at high density in a high-density culture medium while retaining cell viability at or above about 80%. Such cells may be isolated or selected out from the parental population of cells by maintaining the cells at high density ≥about 40, 50, 60, 70, or 80 sequential passages and gradually replacing the proportion of growth medium with the desired high-density culture medium. Optionally, during the process, different pools of cells may be individually propagated and subjected to the selection procedure while simultaneously assessing transfection efficiency and or AAV vector production efficiency, so that clonal population of cells may be selected that can be sustained and grown at high density, transfected with high efficiency, and express high titers of AAV. Clonal populations of cells may be generated using know methods and techniques, for example, flow cytometry sorting and/or single cell cloning. In embodiments, flow cytometry sorting is used to isolate cell clones adapted for high density cell culture and use in the AAV production system. In some embodiments, cell clones adapted for high density cell culture and use in the AAV production system are obtained via single cell cloning and confirmed as single cell clones using known techniques, such as imaging. While it will be readily apparent to the skilled practitioner that a variety of cell types and lineages may be subjected to this selection procedure, it has been determined that cell lineages derived from 293 human embryonic kidney cells are particularly amenable to the selection process for being adapted to high density growth conditions. In some scenarios, cells that are adapted to high density growth culture and amenable for use herein will also be capable of being transfected at high efficiency and/or capable of expressing AAV vector at yield exceeding at least about $5\times10^9$ vg/mL up to about $5\times10^{12}$ vg/mL, between about $1\times10^{10}$ vg/mL up to about $2\times10^{11}$ vg/mL, between about $1\times10^{11}$ vg/mL up to about $1\times10^{11}$ vg/mL, between about $8\times10^{10}$ vg/mL to about $3\times10^{11}$ vg/mL, or between about $5\times10^{10}$ vg/mL to about $2\times10^{11}$ vg/mL of unconcentrated AAV vectors. In some scenarios, cells adapted for high density culture used are capable of being sustained and transfected at densities in the range from about $1\times10^6$ cells/mL to about $2\times10^7$ cells/mL, about $1\times10^6$ cells/mL to about $3\times10^6$ cells/mL, about $2\times10^6$ cells/mL to about $4\times10^6$ cells/mL, or about $2.5\times10^6$ cells/mL to about $4\times10^6$ cells/mL. In some embodiments, cells may be adapted for high density culture and transfected at densities in the range from about $1\times10^6$ cells/mL to about $2\times10^7$ cells/mL, from about $1\times10^6$ cells/mL to about $4\times10^6$ cells/mL, from about $1\times10^6$ cells/mL to about $3\times10^6$ cells/mL, from about $1\times10^6$ cells/mL to about $2\times10^6$ cells/mL.

In some embodiments, the cells are grown in a suspension culture. This includes a cell culture in which the majority or all of the cells in a culture vessel are present in suspension, and the minority or none of the cells in the culture vessel are attached to the vessel surface or to another surface within the vessel. In some embodiments, suspension culture has ≥about 75% of the cells in the culture vessel are in suspension, not attached to a surface on or in the culture vessel. In some embodiments, a suspension culture has ≥about 85% of the cells in the culture vessel are present in suspension, not attached to a surface on or in the culture vessel. In some embodiments, suspension culture has ≥about 95% of the cells in the culture vessel present in suspension, not attached to a surface on or in the culture vessel.

The AAV production system allows the 293 cells, or the cells derived therefrom, to be capable of growing at a density of from about $0.3\times10^6$ cells/mL to about $20\times10^6$ cells/mL with less than 20% cell death after 5 days. In embodiments, the cells are capable of growing at a density of from about $0.3\times10^6$ cells/mL to about $12\times10^6$ cells/mL with less than 20% cell death after 5 days. In some embodiments, the 293 cells as provided herein are capable of growing at a high density, such as from about $0.3\times10^6$ cells/mL to about $20\times10^6$ cells/mL or from about $0.3\times10^6$ cells/mL to about $12\times10^6$ cells/mL, with less than 20% cell death after 6 days, after 7 days, or after 8 days. In embodiments, the 293 cells are capable of growing at a high density, such as from about $0.3\times10^6$ cells/mL to about $20\times10^6$ cells/mL or from about $0.3\times10^6$ cells/mL to about $12\times10^6$ cells/mL, with less than 10% cell death after 5 days, after 6 days, after 7 days, or after 8 days.

Described in another way, the AAV production system provided herein allows the 293 cells, or the cells derived therefrom, to be capable of growing at a density of from about $0.3\times10^6$ cells/mL to about $20\times10^6$ cells/mL with greater than 80% cell viability in the culture after 5 days. In embodiments, the cells are capable of growing at a density of from about $0.3\times10^6$ cells/mL to about $12\times10^6$ cells/mL with greater than 80% cell viability in the culture after 5 days. In some embodiments, the 293 cells as provided herein are capable of growing at a high density, such as from about $0.3 \times 10^6$ cells/mL to about $20 \times 10^6$ cells/mL or from about $0.3 \times 10^6$ cells/mL to about $12 \times 10^6$ cells/mL, with greater than 80% cell viability in the culture after 6 days, after 7 days, or after 8 days. In embodiments, the 293 cells are capable of growing at a high density, such as from about $0.3 \times 10^6$ cells/mL to about $20 \times 10^6$ cells/mL or from about $0.3 \times 10^6$ cells/mL to about $12 \times 10^6$ cells/mL, with greater than 90% cell viability in the culture after 5 days, after 6 days, after 7 days, or after 8 days.

In some embodiments, a suspension culture of 293 cells adapted for high density as provided herein, such as clone 45, subclones of clone 45, and other clones described herein, have at least 10% more viability after 3 days in high density culture than HEK293F cells, Expi293F™ cells, or LV293 (LV-MAX Viral Production Cells) (all available from Thermo Fisher Scientific). In some embodiments, a suspension culture of 293 cells adapted for high density as provided herein have at least 10% more viability than HEK 293F, Expi293F, or LV293 cells after 4 days, after 5 days, after 6 days, after 7 days, or after 8 days of high density culture. In some embodiments, a suspension culture of 293 cells adapted for high density as provided herein have at least 15% more viability than HEK 293F, Expi293F, or LV293 cells after 3 days, after 4 days, after 5 days, after 6 days, after 7 days, or after 8 days of high density culture. In some embodiments, a suspension culture of 293 cells adapted for high density as provided herein have at least 20% more viability than HEK 293F, Expi293F, or LV293 cells after 3 days, after 4 days, after 5 days, 6 days, after 7 days, or after 8 days of high density culture. In some embodiments, a suspension culture of 293 cells adapted for high density as provided herein have at least 25% more viability than HEK 293F, Expi293F, or LV293 cells after 3 days, after 4 days, after 5 days, 6 days, after 7 days, or after 8 days of high density culture. In some embodiments, a suspension culture of 293 cells adapted for high density as provided herein have at least 30% more viability than HEK 293F, Expi293F, or LV293 cells after 3 days, after 4 days, after 5 days, 6 days, after 7 days, or after 8 days of high density culture. In some embodiments, a suspension culture of 293 cells adapted for high density as provided herein have at least 40% more viability than HEK 293F, Expi293F, or LV293 cells after 3 days, after 4 days, after 5 days, 6 days, after 7 days, or after 8 days of high density culture. In embodiments, a suspension culture of 293 cells adapted for high density as provided herein have about 10% to about 30% greater viability than HEK 293F, Expi293F, or LV293 cells after 3 days, after 4 days, after 5 days, after 6 days, after 7 days, or after 8 days of high density culture. In some embodiments, a suspension culture of 293 cells adapted for high density as provided herein have about 20% to about 40% greater viability than HEK 293F, Expi293F, or LV293 cells after 3 days, after 4 days, after 5 days, after 6 days, after 7 days, or after 8 days of high density culture. In some embodiments, a suspension culture of 293 cells adapted for high density as provided herein have about 25% to about 50% greater viability than HEK 293F, Expi293F, or LV293 cells after 3 days, after 4 days, after 5 days, after 6 days, after 7 days, or after 8 days of high density culture.

In embodiments, a suspension culture of 293 cells adapted for high density as provided herein, such as clone 45, subclones of clone 45, and other clones described herein, produce a significantly higher AAV vector yield or titer (vg/mL) than the same amount of HEK293F cells, Expi293F™ cells, or LV293 (LV-MAX Viral Production Cells) (all available from Thermo Fisher Scientific). In some embodiments, a suspension culture of 293 cells adapted for high density as provided herein yield a harvested AAV titer (vg/mL) at least 2 times, at least 3 times, at least 4 times, at least 5 times, at least 6 times, at least 7 times, at least 8 times, at least 10 times, at least 11 times, at least 12 times, at least 14 times, at least 15 times, at least 16 times, at least 18 times, at least 20 times the harvested titer from the same amount of HEK 293F, Expi293F, or LV293 cells. In some embodiments, a suspension culture of 293 cells adapted for high density as provided herein yield a harvested AAV titer (vg/mL) about 2 to about 20 times, about 2 to about 5 times, about 2 to about 10 times, about 5 to about 15 times, about 5 to about 10 times, about 7 to about 20 times, about 10 to about 15 times the AAV vector yield or titer (vg/mL) the harvested titer from same amount of HEK 293F, Expi293F, or LV293 cells.

In embodiments, the cells exhibit limited clumping at very high density, e.g., greater than about $8 \times 10^6$ cells/mL. In embodiments, the cells exhibit limited clumping at greater than about $9 \times 10^6$ cells/mL. In embodiments, the cells exhibit limited clumping at greater than about $10 \times 10^6$ cells/mL. In embodiments, the cells exhibit limited clumping at very high density grown in the culture medium and under conditions as described herein.

In embodiments, the cells have a diameter of between about 15 μm and about 20 μm, such as between about 16 μm and about 19 μm, or between about 16.5 μm and about 19 μm. In embodiments, the cells have a diameter of between about 15 μm and about 20 μm while grown at a density of from about $0.3 \times 10^6$ cells/mL to about $20 \times 10^6$ cells/mL. In embodiments, the cells have a diameter of between about 16 μm and about 19 μm while grown at a density of from about $1 \times 10^6$ cells/mL to about $10 \times 10^6$ cells/mL.

In embodiments, 293 cells adapted to high density growth culture and capable of being transfected at high efficiency and/or capable of expressing AAV vector at yield of about $5 \times 10^9$ vg/mL to about $5 \times 10^{12}$ vg/mL do not express or comprise large T antigen.

A variety of cell culture media may be used to culture the AAV production system cells. Serum free media are often desired by investigators. Any medium, including serum free medium, that supports the growth of the cells described herein may be used. The medium may also be protein free.

A "serum-free medium" (sometimes referred to as "SFM Medium") is a medium that contains no serum (e.g., fetal bovine serum (FBS), calf serum, horse serum, goat serum, human serum, etc.) and is generally designated by the letters SFM. The phrase "protein-free" culture media refers to culture media that contain no protein (e.g., no serum proteins such as serum albumin or attachment factors, nutritive proteins such as growth factors, or metal ion carrier proteins such as transferrin, ceruloplasmin, etc.). In some embodiments, if peptides are present, the peptides are smaller peptides, e.g., di- or tri-peptides. In some embodiments, peptides of deca-peptide length or greater are no more than about 1%, no more than about 0.1%, and no more than about 0.01% of the amino acids present in the protein free medium.

In some embodiments, a high-density culture media may be used, including any culture medium capable of sustaining the growth of mammalian cells. In some embodiments, cells are grown in suspension at densities of up to about $2 \times 10^7$ cells/mL, for example up to about $12 \times 10^6$ cells/mL, while maintaining cell viability in excess of about 80%, such as more than about 90%, and further, maintaining the ability of said suspension cells to be efficiently transfected and express high amounts of AAV vector. The high density culture medium used may vary between different applications and uses, and may depend on the nature of the cell line being used, the nature of the transfection modality selected for transfer of the expression vector into cells, and the amount and nature of any expression enhancers added to the system as described herein. In embodiments, high density culture medium used in the present systems and methods is serum-free and protein-free. In embodiments, the cell culture medium allows the cultivation and growth of suspension cells to a density of up to about $2 \times 10^7$ cells/mL, for example up to about $1.2 \times 10^7$ cells/mL, or between about $2 \times 10^6$ cells/mL to about $1 \times 10^7$ cells/mL. In embodiments, the culture medium used will enable the viral titer produced in the transient expression system to exceed at least $1 \times 10^{10}$ vg/mL up to about $1 \times 10^{12}$ vg/mL, or up to about $2 \times 10^{11}$ vg/mL. In some embodiments, the high density culture medium used will facilitate the transfection of cells at densities in the range of about $1 \times 10^6$ to about $20 \times 10^6$ cells/mL, about $1 \times 10^6$ to about $4 \times 10^6$ cells/mL, or about $2.5 \times 10^6$ to about $3 \times 10^6$ cells/mL.

Examples of high density culture media suitable for use herein include, though are not limited to, HuMEC Basal Serum free Medium, KNOCKOUT™ CTS™ XenoFREE ESC/iPSC Medium, STEMPRO™-34 SFM Medium, STEMPRO™ NSC Medium, ESSENTIAL™-8 Medium, Medium 254, Medium, 106, Medium, 131, Medium, 154, Medium, 171, Medium 171, Medium 200, Medium 231, HeptoZYME-SFM, Human Endothelial-SFM, GIBCO® FREESTYLE™ 293 Expression Medium, Medium 154CF/PRF, Medium 154C, Medium 154 CF, Medium 106, Medium 200PRF, Medium 131, Essential™-6 Medium, STEMPRO™-34 Medium, Gibco® Astrocyte Medium, AIM V® Medium CTS™, AMINOMAX™ C-100 Basal Medium, AMINOMAX™-II Complete Medium, CD FORTICHO™ Medium, CD CHO AGT Medium, CHO-S-SFM Medium, GIBCO® FREESTYLE™ CHO Expression Medium, CD OPTICHO™ Medium, CD CHO Medium, CD DG44 Medium, SF-900™ Medium, EXPI293™ Expression Medium, LHC Basal Medium, LHC-8 Medium, 293 SFM Medium, CD 293 Medium, AEM Growth Medium, PER.C6® Cell Medium, AIM V® Medium, EXPILIFE® Medium, Keratinocyte-SFM Medium, LHC Medium, LHC-8 Medium, LHC-9 Medium, and any derivatives or modifications thereof. In certain nonlimiting embodiments, a high density culture media may be CD FORTICHO™ Medium, CD CHO AGT Medium, CHO-S-SFM Medium, GIBCO® FREESTYLE™ CHO Expression Medium, CD OPTICHO™ Medium, CD CHO Medium, CD DG44 Medium, GIBCO® FREESTYLE™ 293 Expression Medium, EXPI293™ Expression Medium, LV-MAX™ Production Medium, FREESTYLE™ F17 Expression Medium, DYNAMIS™ Medium, BALANCD® HEK293 medium, or a like medium, or a modified version thereof. The culture media may be any media that is suitable (e.g., formulated) for the high density growth, propagation, transfection and maintenance of 293 cells, a 293 cell variant, or any other cells adapted for use in a high density culture system.

The AAV production system also comprises transfection reagent or a composition that facilitates entry of a macromolecule into a cell. In embodiments, the transfection reagent comprises a cationic lipid. In embodiments, the transfection reagent is a cationic lipid as described in U.S. Pat. No. 9,856,496, which is incorporated herein by reference in its entirety.

In some embodiments, a reagent for the introduction of macromolecules into cells can comprise one or more lipids which can be cationic lipids and/or neutral lipids. Preferred lipids include, but are not limited to, N-[1-(2,3-dioleyloxy) propyl]-N,N,N-trimethylamonium chloride (DOTMA), dioleoylphosphatidylcholine (DOPE), 1,2-Bis(oleoyloxy)-3-(4'-trimethylammonio) propane (DOTAP), dihydroxyl-dimyristylspermine tetrahydrochloride (DHDMS), hydroxyl-dimyristylspermine tetrahydrochloride (HDMS), 1,2-dioleoyl-3-(4'-trimethylammonio) butanoyl-sn-glycerol (DOTB), 1,2-dioleoyl-3-succinyl-sn-glycerol choline ester (DOSC), cholesteryl (4'-trimethylammonio) butanoate (ChoTB), cetyltrimethylammonium bromide (CTAB), 1,2-dioleoyl-3-dimethyl-hydroxyethyl ammonium bromide (DORI), 1,2-dioleyloxypropyl-3-dimethyl-hydroxyethyl ammonium bromide (DOME), 1,2-dimyristyloxypropyl-3-dimethylhydroxyethyl ammonium bromide (DMRIE), O,O'-didodecyl-N-[p(2-trimethylammonioethyloxy) benzoyl]-N, N,N-trimethylammonium chloride, spermine conjugated to one or more lipids (for example, 5-carboxyspermylglycine dioctadecylamide (DOGS), N,N$^I$,N$^{II}$,N$^{III}$-tetramethyl-N,N$^I$, N$^{II}$,N$^{III}$-tet-rapalmitylspermine (TM-TPS) and dipalmitoyl-phasphatidylethanolamine 5-carboxyspermylaminde (DPPES)), lipopolylysine (polylysine conjugated to DOPE), TRIS (Tris(hydroxymethyl)aminomethane, tromethamine) conjugated fatty acids (TFAs) and/or peptides such as trilysyl-alanyl-TRIS mono-, di-, and tri-palmitate, (3B-[N-(N', N'-dimethylaminoethane)-carbamoyl] cholesterol (DC-Chol), N-(α-trimethylammonioacetyl)-didodecyl-D-glutamate chloride (TMAG), dimethyl dioctadecylammonium bromide (DDAB), 2,3-dioleyloxy-N-[2(spermine-carboxamido) ethyl]-N,N-dimethyl-1-propanamin-iniumtrinuoroacetate (DOSPA) and combinations thereof. Optionally, the transfection reagent may further comprise at least one additional helper lipid. Helper lipids are known in the art and include, but are not limited to, neutral lipids, preferably selected from the group consisting of DOPE, DOPC and cholesterol. In embodiments, the transfection reagent comprises at least one cationic lipid and at least one neutral lipid.

Those skilled in the art will appreciate that certain combinations of the above mentioned lipids have been shown to be particularly suited for the introduction of nucleic acids into cells for example a 3:1 (w/w) combination of DOSPA and DOPE is available from Life Technologies Corporation, Carlsbad, Calif. under the trade name LIPOFECTAMINE™, a 1:1 (w/w) combination of DOTMA and DOPE is available from Thermo Fisher Scientific under the trade name LIPOFECTIN®, a 1:1 (M/M) combination of DIVIRIE and cholesterol is available from Life Technologies Corporation, Carlsbad, Calif. under the trade name DIVIRIE-C reagent; a 1:1.5 (M/M) combination of TM-TPS and DOPE is available from Life Tech. In some embodiments, the transfection reagent is a cationic lipid transfection reagent. In some embodiments, the transfection reagent is a polymer-based transfection reagent. Other commercially available cationic lipid transfection reagents include, without limitation, TRANSFAST™ (available from Promega Corporation); LYOVEC™ (available from InvivoGen); DOTAP liposomal transfection reagent (available from Roche); TRANSIT® transfection reagents (available from Mirus); and Insect GENEJUICE® Transfection Reagent (EMD Millipore). Additional transfection reagents that may be used herein include, without limitation, LIPOFECTAMINE® 2000, LIPOFECTAMINE® 3000, available from Thermo Fisher Scientific; VIAFECT™ Transfection Reagent, FUGENE® 6 Transfection Reagent, and FUGENE® HD Transfection Reagent, each of which is available from Promega Corporation; and TRANSFEC-TIN™ Lipid Reagent, available from BioRad Laboratories, Inc.

In embodiments, the transfection reagent is combined with a transfection booster. In embodiments, the transfection booster includes a peptide. In embodiments, the transfection booster comprises at least one peptide. In embodiments, the at least one peptide of the transfection booster is a naturally occurring or non-naturally occurring membrane-penetrating peptide. In embodiments, the at least one peptide of the transfection booster comprises a naturally occurring or non-naturally occurring membrane-penetrating peptide sequence. Non-limiting examples of suitable membrane-penetrating peptides and peptide sequences are provided in U.S. Pat. No. 9,856,496, which is incorporated herein by reference in its entirety. In embodiments, the at least one peptide of the transfection booster is a fusogenic peptide, a cell-penetrating peptide, a nuclear localization peptide, a cell surface adhesion peptide, or a plant virus movement peptide. In embodiments, the at least one peptide of the transfection booster comprises a fusogenic peptide sequence, a cell-penetrating peptide sequence, a nuclear localization peptide sequence, a cell surface adhesion peptide sequence, or a plant virus movement peptide sequence. Non-limiting examples of suitable fusogenic, cell-penetrating, nuclear localization, cell surface adhesion, and plant virus movement peptides and peptide sequences are provided in U.S. Pat. Application Publication No. 2017/0253888 A1, which is incorporated herein by reference in its entirety.

In embodiments, the transfection reagent is combined with a transfection booster and the AAV transfer vector to form a transfection complex. In embodiments, the transfection reagent is combined with a transfection booster, the rep/cap plasmid (pRC), the pHelper plasmid (encoding helper virus components), and the AAV transfer vector to form a transfection complex.

In embodiments, the AAV production system includes a lysis buffer. A lysis buffer is a buffer solution used to break open cells and release their contents, e.g., the AAV vector. In embodiments, the lysis buffer is provided at a 5× concentration (five times the final concentration that is contacted with the cells). In embodiments, the lysis buffer is provided at a 10× concentration (ten times the final concentration that is contacted with the cells).

In embodiments, the lysis buffer contains a detergent. In embodiments, the lysis buffer contains at least one detergent selected from CHAP, 3-[(3-cholamidopropyl)dimethylammonio]-1-propanesulfonate (CHAPS), 3-([3-Cholamidopropyl]dimethylammonio)-2-hydroxy-1-propanesulfonate (CHAPSO), N,N-bis-(3-D-Gluconamidopropyl)deoxycholamide (Big CHAP), octylthioglucoside (OTG), and sodium deoxycholate. In embodiments, the lysis buffer contains one detergent selected from CHAP, CHAPS, CHAPSO, Big CHAP, OTG, and sodium deoxycholate. In embodiments, the lysis buffer contains two detergents selected from CHAP, CHAPS, CHAPSO, Big CHAP, OTG, and sodium deoxycholate. In embodiments, the lysis buffer contains three detergents selected from CHAP, CHAPS, CHAPSO, Big CHAP, OTG, and sodium deoxycholate. In embodiments, the lysis buffer contains four or more detergents selected from CHAP, CHAPS, CHAPSO, Big CHAP, OTG, and sodium deoxycholate.

In embodiments, the lysis buffer includes CHAP at a concentration (final concentration contacted with the cells) of between about 0.005% and about 1% (w/v). In embodiments, CHAP is present in the lysis buffer (final concentration contacted with the cells) at a concentration of between about 0.01% and about 1% (w/v). In embodiments, CHAP is present in the lysis buffer (final concentration contacted with the cells) at a concentration of between about 0.01% and about 0.8% (w/v). The concentration may be any value or subrange within the recited ranges, including endpoints.

In embodiments, the lysis buffer includes CHAPS at a concentration (final concentration contacted with the cells) of between about 0.005% and about 1% (w/v). In embodiments, CHAPS is present in the lysis buffer (final concentration contacted with the cells) at a concentration of between about 0.01% and about 1% (w/v). In embodiments, CHAPS is present in the lysis buffer (final concentration contacted with the cells) at a concentration of between about 0.01% and about 0.8% (w/v). The concentration may be any value or subrange within the recited ranges, including endpoints.

In embodiments, the lysis buffer includes CHAPSO at a concentration (final concentration contacted with the cells) of between about 0.005% and about 1% (w/v). In embodiments, CHAPSO is present in the lysis buffer (final concentration contacted with the cells) at a concentration of between about 0.01% and about 1% (w/v). In embodiments, CHAPSO is present in the lysis buffer (final concentration contacted with the cells) at a concentration of between about 0.01% and about 0.8% (w/v). The concentration may be any value or subrange within the recited ranges, including endpoints.

In embodiments, the lysis buffer includes Big CHAP at a concentration (final concentration contacted with the cells) of between about 0.005% and about 1% (w/v). In embodiments, Big CHAP is present in the lysis buffer (final concentration contacted with the cells) at a concentration of between about 0.01% and about 1% (w/v). In embodiments, Big CHAP is present in the lysis buffer (final concentration contacted with the cells) at a concentration of between about 0.01% and about 0.8% (w/v). The concentration may be any value or subrange within the recited ranges, including endpoints.

In embodiments, the lysis buffer includes OTG at a concentration (final concentration contacted with the cells) of between about 0.005% and about 1% (w/v). In embodiments, OTG is present in the lysis buffer (final concentration contacted with the cells) at a concentration of between about 0.01% and about 1% (w/v). In embodiments, OTG is present in the lysis buffer (final concentration contacted with the cells) at a concentration of between about 0.01% and about 0.8% (w/v). The concentration may be any value or subrange within the recited ranges, including endpoints.

In embodiments, the lysis buffer includes sodium deoxycholate at a concentration (final concentration contacted with the cells) of between about 0.005% and about 1% (w/v). In embodiments, sodium deoxycholate is present in the lysis buffer (final concentration contacted with the cells) at a concentration of between about 0.01% and about 1% (w/v). In embodiments, sodium deoxycholate is present in the lysis buffer (final concentration contacted with the cells) at a concentration of between about 0.01% and about 0.8% (w/v). The concentration may be any value or subrange within the recited ranges, including endpoints.

In embodiments, the lysis buffer contains at least one surfactant selected from Triton-100, Triton-alter, NP40, and poloxamer 188 (copolymer of polyoxyethylene and polyoxypropylene; Pluronic® F-68). In embodiments, the lysis buffer contains one surfactant selected from Triton-100, Triton-alter, NP40, and poloxamer 188. In embodiments, the lysis buffer contains two surfactants selected from Triton-100, Triton-alter, NP40, and poloxamer 188. In embodiments, the lysis buffer contains three surfactants selected from Triton-100, Triton-alter, NP40, and poloxamer 188. In embodiments, the lysis buffer contains four surfactants selected from Triton-100, Triton-alter, NP40, and poloxamer 188. Poloxamer 188 has the following formula (I):

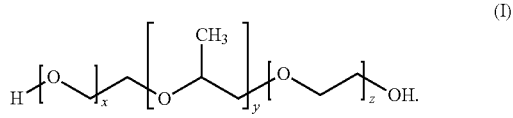

In embodiments, the lysis buffer contains Triton-100 or Triton-alter at a concentration (final concentration contacted with the cells) of between about 0.01% and about 0.1% (w/v). In embodiments, the lysis buffer contains Triton-100 or Triton-alter at a concentration (final concentration contacted with the cells) of between about 0.05% and about 0.1% (w/v). In embodiments, the lysis buffer contains Triton-100 or Triton-alter at a concentration (final concentration contacted with the cells) of between about 0.01% and about 0.05% (w/v). The concentration may be any value or subrange within the recited ranges, including endpoints.

In embodiments, the lysis buffer contains NP40 at a concentration (final concentration contacted with the cells) of between about 0.05% and about 0.5% (w/v). In embodiments, the lysis buffer contains NP40 at a concentration (final concentration contacted with the cells) of between about 0.1% and about 0.5% (w/v). In embodiments, the lysis buffer contains NP40 at a concentration (final concentration contacted with the cells) of between about 0.2% and about 0.5% (w/v). In embodiments, the lysis buffer contains NP40 at a concentration (final concentration contacted with the cells) of between about 0.3% and about 0.5% (w/v). In embodiments, the lysis buffer contains NP40 at a concentration (final concentration contacted with the cells) of between about 0.4% and about 0.5% (w/v). In embodiments, the lysis buffer contains NP40 at a concentration (final concentration contacted with the cells) of between about 0.05% and about 0.4% (w/v). In embodiments, the lysis buffer contains NP40 at a concentration (final concentration contacted with the cells) of between about 0.05% and about 0.3% (w/v). In embodiments, the lysis buffer contains NP40 at a concentration (final concentration contacted with the cells) of between about 0.05% and about 0.2% (w/v). In embodiments, the lysis buffer contains NP40 at a concentration (final concentration contacted with the cells) of between about 0.05% and about 0.1% (w/v). The concentration may be any value or subrange within the recited ranges, including endpoints.

In embodiments, the lysis buffer contains poloxamer 188 at a concentration (final concentration contacted with the cells) of between about 0.08% and about 0.2% (w/v). In embodiments, the lysis buffer contains poloxamer 188 at a concentration (final concentration contacted with the cells) of between about 0.09% and about 0.2% (w/v). In embodiments, the lysis buffer contains poloxamer 188 at a concentration (final concentration contacted with the cells) of between about 0.1% and about 0.2% (w/v). In embodiments, the lysis buffer contains poloxamer 188 at a concentration (final concentration contacted with the cells) of between about 0.08% and about 0.15% (w/v). In embodiments, the lysis buffer contains poloxamer 188 at a concentration (final concentration contacted with the cells) of between about 0.08% and about 0.1% (w/v). The concentration may be any value or subrange within the recited ranges, including endpoints.

In embodiments, the lysis buffer contains at least one salt. In embodiments, the salt is sodium citrate, sodium chloride, potassium chloride, ammonium sulfate, ammonium phosphate, and/or a sodium phosphate (e.g., sodium dihydrogen phosphate, disodium phosphate, trisodium phosphate).

In embodiments, the lysis buffer contains sodium citrate at a concentration (final concentration contacted with the cells) of between about 1 mM and about 1000 mM. In embodiments, the lysis buffer contains sodium citrate at a concentration (final concentration contacted with the cells) of between about 1 mM and about 500 mM. In embodiments, the lysis buffer contains sodium citrate at a concentration (final concentration contacted with the cells) of between about 1 mM and about 400 mM. In embodiments, the lysis buffer contains sodium citrate at a concentration (final concentration contacted with the cells) of between about 1 mM and about 300 mM. In embodiments, the lysis buffer contains sodium citrate at a concentration (final concentration contacted with the cells) of between about 1 mM and about 200 mM. In embodiments, the lysis buffer contains sodium citrate at a concentration (final concentration contacted with the cells) of between about 1 mM and about 100 mM. In embodiments, the lysis buffer contains sodium citrate at a concentration (final concentration contacted with the cells) of between about 10 mM and about 1000 mM. In embodiments, the lysis buffer contains sodium citrate at a concentration (final concentration contacted with the cells) of between about 10 mM and about 500 mM. In embodiments, the lysis buffer contains sodium citrate at a concentration (final concentration contacted with the cells) of between about 10 mM and about 400 mM. In embodiments, the lysis buffer contains sodium citrate at a concentration (final concentration contacted with the cells) of between about 10 mM and about 300 mM. In embodiments, the lysis buffer contains sodium citrate at a concentration (final concentration contacted with the cells) of between about 10 mM and about 200 mM. In embodiments, the lysis buffer contains sodium citrate at a concentration (final concentration contacted with the cells) of between about 10 mM and about 100 mM. The concentration may be any value or subrange within the recited ranges, including endpoints.

In embodiments, the lysis buffer contains sodium chloride at a concentration (final concentration contacted with the cells) of between about 1 mM and about 1000 mM. In embodiments, the lysis buffer contains sodium chloride at a concentration (final concentration contacted with the cells) of between about 1 mM and about 500 mM. In embodiments, the lysis buffer contains sodium chloride at a concentration (final concentration contacted with the cells) of between about 1 mM and about 400 mM. In embodiments, the lysis buffer contains sodium chloride at a concentration (final concentration contacted with the cells) of between about 1 mM and about 300 mM. In embodiments, the lysis buffer contains sodium chloride at a concentration (final concentration contacted with the cells) of between about 1 mM and about 200 mM. In embodiments, the lysis buffer contains sodium chloride at a concentration (final concentration contacted with the cells) of between about 1 mM and about 100 mM. In embodiments, the lysis buffer contains sodium chloride at a concentration (final concentration contacted with the cells) of between about 10 mM and about 1000 mM. In embodiments, the lysis buffer contains sodium chloride at a concentration (final concentration contacted with the cells) of between about 10 mM and about 500 mM.

In embodiments, the lysis buffer contains sodium chloride at a concentration (final concentration contacted with the cells) of between about 10 mM and about 400 mM. In embodiments, the lysis buffer contains sodium chloride at a concentration (final concentration contacted with the cells) of between about 10 mM and about 300 mM. In embodiments, the lysis buffer contains sodium chloride at a concentration (final concentration contacted with the cells) of between about 10 mM and about 200 mM. In embodiments, the lysis buffer contains sodium chloride at a concentration (final concentration contacted with the cells) of between about 10 mM and about 100 mM. The concentration may be any value or subrange within the recited ranges, including endpoints.

In embodiments, the lysis buffer contains ammonium phosphate at a concentration (final concentration contacted with the cells) of between about 0.5 mM and about 500 mM. In embodiments, the lysis buffer contains ammonium phosphate at a concentration (final concentration contacted with the cells) of between about 0.5 mM and about 250 mM. In embodiments, the lysis buffer contains ammonium phosphate at a concentration (final concentration contacted with the cells) of between about 0.5 mM and about 100 mM. In embodiments, the lysis buffer contains ammonium phosphate at a concentration (final concentration contacted with the cells) of between about 0.5 mM and about 50 mM. In embodiments, the lysis buffer contains ammonium phosphate at a concentration (final concentration contacted with the cells) of between about 0.5 mM and about 10 mM. In embodiments, the lysis buffer contains ammonium phosphate at a concentration (final concentration contacted with the cells) of between about 1 mM and about 500 mM. In embodiments, the lysis buffer contains ammonium phosphate at a concentration (final concentration contacted with the cells) of between about 1 mM and about 250 mM. In embodiments, the lysis buffer contains ammonium phosphate at a concentration (final concentration contacted with the cells) of between about 1 mM and about 100 mM. In embodiments, the lysis buffer contains ammonium phosphate at a concentration (final concentration contacted with the cells) of between about 1 mM and about 50 mM. In embodiments, the lysis buffer contains ammonium phosphate at a concentration (final concentration contacted with the cells) of between about 1 mM and about 10 mM. The concentration may be any value or subrange within the recited ranges, including endpoints.

In embodiments, the lysis buffer contains a sodium phosphate (e.g., sodium dihydrogen phosphate, disodium phosphate, trisodium phosphate) at a concentration (final concentration contacted with the cells) of between about 0.5 mM and about 500 mM. In embodiments, the lysis buffer contains a sodium phosphate (e.g., sodium dihydrogen phosphate, disodium phosphate, trisodium phosphate) at a concentration (final concentration contacted with the cells) of between about 0.5 mM and about 250 mM. In embodiments, the lysis buffer contains a sodium phosphate (e.g., sodium dihydrogen phosphate, disodium phosphate, trisodium phosphate) at a concentration (final concentration contacted with the cells) of between about 0.5 mM and about 100 mM. In embodiments, the lysis buffer contains a sodium phosphate (e.g., sodium dihydrogen phosphate, disodium phosphate, trisodium phosphate) at a concentration (final concentration contacted with the cells) of between about 0.5 mM and about 50 mM. In embodiments, the lysis buffer contains a sodium phosphate (e.g., sodium dihydrogen phosphate, disodium phosphate, trisodium phosphate) at a concentration (final concentration contacted with the cells) of between about 0.5 mM and about 10 mM. In embodiments, the lysis buffer contains a sodium phosphate (e.g., sodium dihydrogen phosphate, disodium phosphate, trisodium phosphate) at a concentration (final concentration contacted with the cells) of between about 1 mM and about 500 mM. In embodiments, the lysis buffer contains a sodium phosphate (e.g., sodium dihydrogen phosphate, disodium phosphate, trisodium phosphate) at a concentration (final concentration contacted with the cells) of between about 1 mM and about 250 mM. In embodiments, the lysis buffer contains a sodium phosphate (e.g., sodium dihydrogen phosphate, disodium phosphate, trisodium phosphate) at a concentration (final concentration contacted with the cells) of between about 1 mM and about 100 mM. In embodiments, the lysis buffer contains a sodium phosphate (e.g., sodium dihydrogen phosphate, disodium phosphate, trisodium phosphate) at a concentration (final concentration contacted with the cells) of between about 1 mM and about 50 mM. In embodiments, the lysis buffer contains a sodium phosphate (e.g., sodium dihydrogen phosphate, disodium phosphate, trisodium phosphate) at a concentration (final concentration contacted with the cells) of between about 1 mM and about 10 mM. The concentration may be any value or subrange within the recited ranges, including endpoints.

In embodiments, the lysis buffer contains a chelating agent. In embodiments, the chelating agent is ethylenediaminetetraacetic acid (EDTA), tri-potassium EDTA, and/or ethylene glycol tetraacetic acid (EGTA).

In embodiments, the lysis buffer contains EDTA at a concentration (final concentration contacted with the cells) of between about 0.1 mM and about 50 mM. In embodiments, the lysis buffer contains EDTA at a concentration (final concentration contacted with the cells) of between about 0.1 mM and about 40 mM. In embodiments, the lysis buffer contains EDTA at a concentration (final concentration contacted with the cells) of between about 0.1 mM and about 30 mM. In embodiments, the lysis buffer contains EDTA at a concentration (final concentration contacted with the cells) of between about 0.1 mM and about 20 mM. In embodiments, the lysis buffer contains EDTA at a concentration (final concentration contacted with the cells) of between about 0.1 mM and about 10 mM. In embodiments, the lysis buffer contains EDTA at a concentration (final concentration contacted with the cells) of between about 0.1 mM and about 5 mM. In embodiments, the lysis buffer contains EDTA at a concentration (final concentration contacted with the cells) of between about 1 mM and about 50 mM. In embodiments, the lysis buffer contains EDTA at a concentration (final concentration contacted with the cells) of between about 1 mM and about 40 mM. In embodiments, the lysis buffer contains EDTA at a concentration (final concentration contacted with the cells) of between about 1 mM and about 30 mM. In embodiments, the lysis buffer contains EDTA at a concentration (final concentration contacted with the cells) of between about 1 mM and about 20 mM. In embodiments, the lysis buffer contains EDTA at a concentration (final concentration contacted with the cells) of between about 1 mM and about 10 mM. In embodiments, the lysis buffer contains EDTA at a concentration (final concentration contacted with the cells) of between about 1 mM and about 5 mM. The concentration may be any value or subrange within the recited ranges, including endpoints.

In embodiments, the lysis buffer contains tri-potassium EDTA at a concentration (final concentration contacted with the cells) of between about 0.1 mM and about 50 mM. In embodiments, the lysis buffer contains tri-potassium EDTA at a concentration (final concentration contacted with the cells) of between about 0.1 mM and about 40 mM. In embodiments, the lysis buffer contains tri-potassium EDTA at a concentration (final concentration contacted with the cells) of between about 0.1 mM and about 30 mM. In embodiments, the lysis buffer contains tri-potassium EDTA at a concentration (final concentration contacted with the cells) of between about 0.1 mM and about 20 mM. In embodiments, the lysis buffer contains tri-potassium EDTA at a concentration (final concentration contacted with the cells) of between about 0.1 mM and about 10 mM. In embodiments, the lysis buffer contains tri-potassium EDTA at a concentration (final concentration contacted with the cells) of between about 0.1 mM and about 5 mM. In embodiments, the lysis buffer contains tri-potassium EDTA at a concentration (final concentration contacted with the cells) of between about 1 mM and about 50 mM. In embodiments, the lysis buffer contains tri-potassium EDTA at a concentration (final concentration contacted with the cells) of between about 1 mM and about 40 mM. In embodiments, the lysis buffer contains tri-potassium EDTA at a concentration (final concentration contacted with the cells) of between about 1 mM and about 30 mM. In embodiments, the lysis buffer contains tri-potassium EDTA at a concentration (final concentration contacted with the cells) of between about 1 mM and about 20 mM. In embodiments, the lysis buffer contains tri-potassium EDTA at a concentration (final concentration contacted with the cells) of between about 1 mM and about 10 mM. In embodiments, the lysis buffer contains tri-potassium EDTA at a concentration (final concentration contacted with the cells) of between about 1 mM and about 5 mM. The concentration may be any value or subrange within the recited ranges, including endpoints.

In embodiments, the lysis buffer contains EGTA at a concentration (final concentration contacted with the cells) of between about 0.1 mM and about 50 mM. In embodiments, the lysis buffer contains EGTA at a concentration (final concentration contacted with the cells) of between about 0.1 mM and about 40 mM. In embodiments, the lysis buffer contains EGTA at a concentration (final concentration contacted with the cells) of between about 0.1 mM and about 30 mM. In embodiments, the lysis buffer contains EGTA at a concentration (final concentration contacted with the cells) of between about 0.1 mM and about 20 mM. In embodiments, the lysis buffer contains EGTA at a concentration (final concentration contacted with the cells) of between about 0.1 mM and about 10 mM. In embodiments, the lysis buffer contains EGTA at a concentration (final concentration contacted with the cells) of between about 0.1 mM and about 5 mM. In embodiments, the lysis buffer contains EGTA at a concentration (final concentration contacted with the cells) of between about 1 mM and about 50 mM. In embodiments, the lysis buffer contains EGTA at a concentration (final concentration contacted with the cells) of between about 1 mM and about 40 mM. In embodiments, the lysis buffer contains EGTA at a concentration (final concentration contacted with the cells) of between about 1 mM and about 30 mM. In embodiments, the lysis buffer contains EGTA at a concentration (final concentration contacted with the cells) of between about 1 mM and about 20 mM. In embodiments, the lysis buffer contains EGTA at a concentration (final concentration contacted with the cells) of between about 1 mM and about 10 mM. In embodiments, the lysis buffer contains EGTA at a concentration (final concentration contacted with the cells) of between about 1 mM and about 5 mM. The concentration may be any value or subrange within the recited ranges, including endpoints.

In embodiments, the lysis buffer contains at least one additional compound. For example, the lysis buffer may contain 3-(1-pyridinio) propanesulfonate (NDSB 201; Non-detergent Sulfobetaine 201). In embodiments, the lysis buffer contains Tris-HCl. In embodiments, the lysis buffer contains citric acid. In embodiments, the lysis buffer contains sodium hydroxide (NaOH).

In embodiments, the lysis buffer contains NDSB-201 at a concentration (final concentration contacted with the cells) of between about 0.5 M to about 1 M. In embodiments, the lysis buffer contains NDSB-201 at a concentration (final concentration contacted with the cells) of between about 0.6 M to about 1 M. In embodiments, the lysis buffer contains NDSB-201 at a concentration (final concentration contacted with the cells) of between about 0.7 M to about 1 M. In embodiments, the lysis buffer contains NDSB-201 at a concentration (final concentration contacted with the cells) of between about 0.8 M to about 1 M. In embodiments, the lysis buffer contains NDSB-201 at a concentration (final concentration contacted with the cells) of between about 0.9 M to about 1 M. In embodiments, the lysis buffer contains NDSB-201 at a concentration (final concentration contacted with the cells) of between about 0.5 M to about 0.9 M. In embodiments, the lysis buffer contains NDSB-201 at a concentration (final concentration contacted with the cells) of between about 0.5 M to about 0.8 M. In embodiments, the lysis buffer contains NDSB-201 at a concentration (final concentration contacted with the cells) of between about 0.5 M to about 0.7 M. In embodiments, the lysis buffer contains NDSB-201 at a concentration (final concentration contacted with the cells) of between about 0.5 M to about 0.6 M. The concentration may be any value or subrange within the recited ranges, including endpoints.

In embodiments, the lysis buffer contains Tris-HCl at a concentration (final concentration contacted with the cells) of between about 5 mM to about 20 mM. In embodiments, the lysis buffer contains Tris-HCl at a concentration (final concentration contacted with the cells) of between about 6 mM to about 20 mM. In embodiments, the lysis buffer contains Tris-HCl at a concentration (final concentration contacted with the cells) of between about 8 mM to about 20 mM. In embodiments, the lysis buffer contains Tris-HCl at a concentration (final concentration contacted with the cells) of between about 10 mM to about 20 mM. In embodiments, the lysis buffer contains Tris-HCl at a concentration (final concentration contacted with the cells) of between about 12 mM to about 20 mM. In embodiments, the lysis buffer contains Tris-HCl at a concentration (final concentration contacted with the cells) of between about 14 mM to about 20 mM. In embodiments, the lysis buffer contains Tris-HCl at a concentration (final concentration contacted with the cells) of between about 15 mM to about 20 mM. In embodiments, the lysis buffer contains Tris-HCl at a concentration (final concentration contacted with the cells) of between about 10 mM to about 20 mM. In embodiments, the lysis buffer contains Tris-HCl at a concentration (final concentration contacted with the cells) of between about 12 mM to about 20 mM. In embodiments, the lysis buffer contains Tris-HCl at a concentration (final concentration contacted with the cells) of between about 15 mM to about 20 mM. The concentration may be any value or subrange within the recited ranges, including endpoints.

In embodiments, the lysis buffer contains citric acid at a concentration (final concentration contacted with the cells) of between about 20 mM to about 100 mM. In embodiments, the lysis buffer contains citric acid at a concentration (final concentration contacted with the cells) of between about 40 mM to about 100 mM. In embodiments, the lysis buffer contains citric acid at a concentration (final concentration contacted with the cells) of between about 50 mM to about 100 mM. In embodiments, the lysis buffer contains citric acid at a concentration (final concentration contacted with the cells) of between about 60 mM to about 100 mM. In embodiments, the lysis buffer contains citric acid at a concentration (final concentration contacted with the cells) of between about 80 mM to about 100 mM. In embodiments, the lysis buffer contains citric acid at a concentration (final concentration contacted with the cells) of between about 20 mM to about 80 mM. In embodiments, the lysis buffer contains citric acid at a concentration (final concentration contacted with the cells) of between about 20 mM to about 60 mM. In embodiments, the lysis buffer contains citric acid at a concentration (final concentration contacted with the cells) of between about 20 mM to about 40 mM. The concentration may be any value or subrange within the recited ranges, including endpoints.

In embodiments, the lysis buffer contains NaOH at a concentration (final concentration contacted with the cells) of between about 1 mM to about 50 mM. In embodiments, the lysis buffer contains NaOH at a concentration (final concentration contacted with the cells) of between about 10 mM to about 50 mM. In embodiments, the lysis buffer contains NaOH at a concentration (final concentration contacted with the cells) of between about 20 mM to about 50 mM. In embodiments, the lysis buffer contains NaOH at a concentration (final concentration contacted with the cells) of between about 30 mM to about 50 mM. In embodiments, the lysis buffer contains NaOH at a concentration (final concentration contacted with the cells) of between about 40 mM to about 50 mM. In embodiments, the lysis buffer contains NaOH at a concentration (final concentration contacted with the cells) of between about 1 mM to about 40 mM. In embodiments, the lysis buffer contains NaOH at a concentration (final concentration contacted with the cells) of between about 1 mM to about 30 mM. In embodiments, the lysis buffer contains NaOH at a concentration (final concentration contacted with the cells) of between about 1 mM to about 20 mM. In embodiments, the lysis buffer contains NaOH at a concentration (final concentration contacted with the cells) of between about 1 mM to about 10 mM. The concentration may be any value or subrange within the recited ranges, including endpoints.

The AAV production system also comprises an AAV production enhancer (AAV enhancer). The AAV enhancer comprises one or more of a histone deacetylase (HDAC) inhibitor, sodium proprionate, sodium butyrate, theobromine, and caffeine.

In embodiments, the HDAC inhibitor is selected from apicidin, belinostat, CI-994, CRA-024781, curcumin, panobinostat, sodium butyrate, sodium phenylbutyrate, suberoylanilide hydroxamic acid, trichostatin A, and valproic acid. In embodiments, the HDAC inhibitor is sodium butyrate, sodium phenylbutyrate, trichostatin A, and/or valproic acid.

In embodiments, the sodium propionate and/or HDAC inhibitor are provided in water. In embodiments, the caffeine is provided in cell culture expression medium, such as Expi293™ expression medium.

In embodiments, sodium propionate is included at a concentration (final concentration contacted with the cells) from about 1 mM to about 50 mM. In embodiments, sodium propionate is included at from about 1 mM to 40 mM. In embodiments, sodium propionate is included at from about 1 mM to 30 mM. In embodiments, sodium propionate is included at from about 1 mM to 20 mM. In embodiments, sodium propionate is included at from about 1 mM to 10 mM. In embodiments, sodium propionate is included at from about 1 mM to 5 mM. In embodiments, sodium propionate is included at from about 2 mM to 30 mM. In embodiments, sodium propionate is included at from about 2 mM to 20 mM. In embodiments, sodium propionate is included at from about 2 mM to 10 mM. In embodiments, sodium propionate is included at from about 2 mM to 5 mM. The concentration may be any value or subrange within the recited ranges, including endpoints.

In embodiments, the HDAC inhibitor is included at a concentration (final concentration contacted with the cells) from about 0.1 mM to about 100 mM. In embodiments, the HDAC inhibitor is included at a concentration from about 0.1 mM to about 75 mM. In embodiments, the HDAC inhibitor is included at a concentration from about 0.1 mM to about 50 mM. In embodiments, the HDAC inhibitor is included at a concentration from about 0.1 mM to about 25 mM. In embodiments, the HDAC inhibitor is included at a concentration from about 0.1 mM to about 10 mM. In embodiments, the HDAC inhibitor is included at a concentration from about 0.1 mM to about 9 mM. In embodiments, the HDAC inhibitor is included at a concentration from about 0.1 mM to about 8 mM. In embodiments, the HDAC inhibitor is included at a concentration from about 0.1 mM to about 7 mM. In embodiments, the HDAC inhibitor is included at a concentration from about 0.1 mM to about 6 mM. In embodiments, the HDAC inhibitor is included at a concentration from about 0.1 mM to about 5 mM. In embodiments, the HDAC inhibitor is included at a concentration from about 1 mM to about 100 mM. In embodiments, the HDAC inhibitor is included at a concentration from about 1 mM to about 50 mM. In embodiments, the HDAC inhibitor is included at a concentration from about 1 mM to about 25 mM. In embodiments, the HDAC inhibitor is included at a concentration from about 1 mM to about 10 mM. In embodiments, the HDAC inhibitor is included at a concentration from about 1 mM to about 9 mM. In embodiments, the HDAC inhibitor is included at a concentration from about 1 mM to about 8 mM. In embodiments, the HDAC inhibitor is included at a concentration from about 1 mM to about 7 mM. In embodiments, the HDAC inhibitor is included at a concentration from about 1 mM to about 6 mM. In embodiments, the HDAC inhibitor is included at a concentration from about 1 mM to about 5 mM. The concentration may be any value or subrange within the recited ranges, including endpoints.

In embodiments, caffeine is included at a concentration (final concentration contacted with the cells) from about 0.1 mM to about 50 mM. In embodiments, caffeine is included at a concentration from about 0.1 mM to about 25 mM. In embodiments, caffeine is included at a concentration from about 0.1 mM to about 15 mM. In embodiments, caffeine is included at a concentration from about 0.1 mM to about 10 mM. In embodiments, caffeine is included at a concentration from about 0.1 mM to about 9 mM. In embodiments, caffeine is included at a concentration from about 0.1 mM to about 8 mM. In embodiments, caffeine is included at a concentration from about 0.1 mM to about 7 mM. In embodiments, caffeine is included at a concentration from about 0.1 mM to about 6 mM. In embodiments, caffeine is included at a concentration from about 0.1 mM to about 5 mM. In embodiments, caffeine is included at a concentration from about 0.1 mM to about 4 mM. In embodiments, caffeine is included at a concentration from about 0.1 mM to about 3 mM. In embodiments, caffeine is included at a concentration from about 0.1 mM to about 2 mM. In embodiments, caffeine is included at a concentration from about 0.5 mM to about 50 mM. In embodiments, caffeine is included at a concentration from about 0.5 mM to about 10 mM. In embodiments, caffeine is included at a concentration from about 0.5 mM to about 5 mM. In embodiments, caffeine is included at a concentration from about 0.5 mM to about 4 mM. In embodiments, caffeine is included at a concentration from about 0.5 mM to about 3 mM. In embodiments, caffeine is included at a concentration from about 0.5 mM to about 2 mM. The concentration may be any value or subrange within the recited ranges, including endpoints.

In some embodiments, the AAV enhancer is added at one or more than one time point, such as at the time of transfection (about hour 0) until about 48 hours after transfection. The AAV enhancer may be added at about 1 hour to about 16 hours after transfection to boost cell packaging of AAV vectors. In some embodiments, the AAV enhancer may be added at the time of transfection. In some embodiments, the AAV enhancer may be added at the time of transfection and at about 1 hour to about 16 hours after transfection. In some embodiments, AAV enhancer may be added from about 4 to 5 hours after transfection. In some embodiments, AAV enhancer may be added from about 0, 1, 2, 3, 4, 5, 6, 7, 8, 9, 10, 11, 12, 16, 24, 36, or 48 hours after transfection. The AAV enhancer may be added at any time (or subrange) within the recited ranges, including endpoints.

The design and production of AAV vectors is known in the art. See, e.g., U.S. Pat. Nos. 5,354,678; 6,759,237; 5,753,500; and 5,474,935. For proper packaging of AAV, packaging plasmids can be used. These plasmids encode genes that are necessary for packaging of AAV vectors. Such genes include genes expressing the capsid protein (cap) and the replication (rep) gene. Alternatively, the genes may be stably expressed by the cells. The AAV genes can be any from any serotype AAV, including but not limited to serotype 1, 2, 3, 4, 5, 6, 7, 8, 9, DJ or DJ/8. Packaging plasmids encoding AAV rep and cap genes are often referred to as pAAV-RC, pRep/Cap or pRC plasmids. AAV transfer vectors, packaging plasmids, packaging cell lines, and other products for AAV production are commercially available, for example from Cell Biolabs, Inc., Vector Biolabs, Addgene, Clontech, and Thermo Fisher Scientific.

In embodiments, helper virus (e.g., from adenovirus or herpesvirus) components are required for proper function of the AAV production system. Helper virus components may be present on plasmids (and often referred to as pAAV-Helper or pHelper plasmid) or otherwise present in the cells. Helper virus components include, but are not limited to, E1A, E1B, E2A, E4, and/or VA.

Provided herein is a kit for adeno-associated virus (AAV) production. In embodiments, the kit includes 293 cells adapted for high density suspension culture; an AAV production enhancer; a transfection reagent comprising a cationic lipid; and a cell culture media that supports growth and expansion of the 293 cells. In embodiments, the transfection reagent contains a cationic lipid and a peptide. In embodiments, the transfection reagent comprises at least one cationic lipid and at least one neutral lipid. In embodiments, the AAV production enhancer comprises one or more of a HDAC inhibitor, sodium proprionate, sodium butyrate, theobromine and caffeine. In embodiments, the 293 cells do not comprise large T antigen.

In embodiments, the kit also includes a transfection booster. In embodiments, the transfection booster contains a peptide. In embodiments, the transfection booster contains a membrane-penetrating peptide.

In embodiments, the kit also includes a lysis buffer. In embodiments, the lysis buffer contains at least one surfactant. In embodiments, the surfactant is Triton-100, Triton-alter, NP-40, poloxamer 188, and/or NDSB-201. In embodiments, the lysis buffer contains Tris-HCl, sodium citrate, Tricine HCL, sodium chloride, citric acid, EDTA, tri-potassium EDTA, sodium hydroxide, and/or sodium dihydrogen phosphate. In embodiments, the lysis buffer includes at least one detergent. In embodiments, the detergent is CHAP, CHAPS, CHAPSO, big CHAP, deoxyl Big CHAP, Triton X-114, octylthioglucoside, and/or sodium deoxycholate.

Methods for Use of an Adeno Associated Virus (AAV) Production System

An AAV production system as described herein can be used to produce AAV vectors. In embodiments, the AAV vectors are produced at high titer.

In an aspect is provided a method for AAV vector production, including: (i) culturing mammalian cells; (ii) transfecting the mammalian cells with an AAV transfer vector using a transfection reagent; and (iii) culturing the transfected cells in suspension culture for a period of time sufficient for expression of the AAV vector. In embodiments, the mammalian cells are cultured in suspension culture. In embodiments, the method includes harvesting AAV from the transfected AAV cell culture. In embodiments, the transfection step includes contacting the cells with a transfection booster. In embodiments, the cells are contacted with an enhancer after transfection.

In embodiments, the transfection reagent is combined with the AAV transfer vector to form a DNA/transfection reagent complex prior to addition to the cells. In embodiments, the transfection reagent is combined with the AAV transfer vector, the pRep/Cap plasmid and the pHelper plasmid to form a DNA/transfection reagent complex prior to addition to the cells.

In other embodiments, the transfection booster is combined with the AAV transfer vector to form a DNA/transfection booster mixture and then the transfection reagent is combined with the DNA/transfection booster mixture prior to addition to the cells. In embodiments, the transfection booster is combined with the AAV transfer vector, the pRep/Cap plasmid and the pHelper plasmid to form a DNA/transfection booster mixture and then the transfection reagent is combined with the DNA/transfection booster mixture prior to addition to the cells. In some embodiments, the DNA and transfection booster are combined in a tube, the transfection reagent is diluted into media in a second tube and then the diluted transfection reagent is added to the DNA/transfection booster mixture to form a DNA/transfection booster/transfection reagent complex. In other embodiments, the DNA and transfection booster are combined in a tube and then the transfection reagent is added to the same tube to form a DNA/transfection booster/transfection reagent complex. In other embodiments, the DNA and transfection reagent are combined in a tube and then the transfection booster is added to the same tube to form a DNA/transfection booster/transfection reagent complex.

In embodiments, the transfection booster is used at a ratio of between 5:1 and about 1:5 (volume/weight) transfection booster:DNA. In embodiments, the transfection reagent is combined with a transfection booster, the rep/cap plasmid (pRC), the pHelper plasmid (encoding helper virus components), and the AAV transfer vector to form a transfection complex.

In embodiments, the AAV are harvested using a lysis buffer. In embodiments, the cells are not centrifuged prior to harvesting AAV. In embodiments, the lysis buffer is added directly to the transfected cell culture (e.g., the cells and culture medium).

In embodiments, the crude culture lysate containing AAV is filtered prior to downstream processing, such as nuclease treatment and purification processes. In embodiments, the crude lysate is mixed with diatomaceous earth and then the mixture is passed through a filter, for example a 2 micron filter, to recover the harvested AAV. Alternatively, a cellulose filtration step may be used with the crude lysate to produce an AAV preparation ready for downstream processing. Subjecting the crude AAV lysate to such a filtration step, for example with diatomaceous earth, cellulose or equivalent, reduces the number of filters needed and reduces the filtration and processing time of AAV lysate prior to purification processes.

In embodiments, the cells are cultured in a bioreactor. In embodiments, the cells are cultured in a flask.

In embodiments, the method includes titering the harvested AAV. The AAV may be titered using any method. In embodiments, the AAV is titered using polymerase chain reaction (PCR). In embodiments, the AAV is titered using quantitative PCR (qPCR). In embodiments, the AAV is titered using digital droplet PCR. In embodiments, the AAV is titered using ELISA. In embodiments, the AAV is titered using a viral titer kit, e.g., QUICKTITER™ AAV Quantitation Kit (Cell BioLabs, Inc.); see also, U.S. Pat. No. 6,841,357, which is incorporated herein by reference in its entirety. In embodiments, the AAV is titered by determining the concentration of viral particles that can transduce cells (infectious titer), e.g. by cell transduction assay. In embodiments, the AAV is titered using DNA dot blotting.

In embodiments, the harvested AAV has a titer of at least about $1\times10^{10}$ viral genomes per milliliter (vg/mL). In embodiments, the harvested AAV has a titer of at least about $2\times10^{10}$ vg/mL. In embodiments, the harvested AAV has a titer of at least about $3\times10^{10}$ vg/mL. In embodiments, the harvested AAV has a titer of at least about $4\times10^{10}$ vg/mL. In embodiments, the harvested AAV has a titer of at least about $5\times10^{10}$ vg/mL. In embodiments, the harvested AAV has a titer of at least about $6\times10^{10}$ vg/mL. In embodiments, the harvested AAV has a titer of at least about $7\times10^{10}$ vg/mL. In embodiments, the harvested AAV has a titer of at least about $8\times10^{10}$ vg/mL. In embodiments, the harvested AAV has a titer of at least about $9\times10^{10}$ vg/mL. In embodiments, the harvested AAV has a titer of at least about $1\times10^{11}$ vg/mL. In embodiments, the harvested AAV has a titer of at least about $2\times10^{11}$ vg/mL. In embodiments, the harvested AAV has a titer of at least about $3\times10^{11}$ vg/mL. In embodiments, the harvested AAV has a titer of at least about $4\times10^{11}$ vg/mL. In embodiments, the harvested AAV has a titer of at least about $5\times10^{11}$ vg/mL. In embodiments, the harvested AAV has a titer of at least about $6\times10^{11}$ vg/mL. In embodiments, the harvested AAV has a titer of at least about $7\times10^{11}$ vg/mL. In embodiments, the harvested AAV has a titer of at least about $8\times10^{11}$ vg/mL. In embodiments, the harvested AAV has a titer of at least about $9\times10^{11}$ vg/mL.

In embodiments, the harvested AAV has a titer between about $1\times10^{10}$ vg/mL and about $1\times10^{12}$ vg/mL. In embodiments, the harvested AAV has a titer between about $2\times10^{10}$ vg/mL and about $1\times10^{12}$ vg/mL. In embodiments, the harvested AAV has a titer between about $3\times10^{10}$ vg/mL and about $1\times10^{12}$ vg/mL. In embodiments, the harvested AAV has a titer between about $4\times10^{10}$ vg/mL and about $1\times10^{12}$ vg/mL. In embodiments, the harvested AAV has a titer between about $5\times10^{10}$ vg/mL and about $1\times10^{12}$ vg/mL. In embodiments, the harvested AAV has a titer between about $6\times10^{10}$ vg/mL and about $1\times10^{12}$ vg/mL. In embodiments, the harvested AAV has a titer between about $7\times10^{10}$ vg/mL and about $1\times10^{12}$ vg/mL. In embodiments, the harvested AAV has a titer between about $8\times10^{10}$ vg/mL and about $1\times10^{12}$ vg/mL. In embodiments, the harvested AAV has a titer between about $9\times10^{10}$ vg/mL and about $1\times10^{12}$ vg/mL. In embodiments, the harvested AAV has a titer between about $1\times10^{11}$ vg/mL and about $1\times10^{12}$ vg/mL. In embodiments, the harvested AAV has a titer between about $2\times10^{11}$ vg/mL and about $1\times10^{12}$ vg/mL. In embodiments, the harvested AAV has a titer between about $3\times10^{11}$ vg/mL and about $1\times10^{12}$ vg/mL. In embodiments, the harvested AAV has a titer between about $4\times10^{11}$ vg/mL and about $1\times10^{12}$ vg/mL. In embodiments, the harvested AAV has a titer between about $5\times10^{11}$ vg/mL and about $1\times10^{12}$ vg/mL. In embodiments, the harvested AAV has a titer between about $2\times10^{10}$ vg/mL and about $9\times10^{11}$ vg/mL. In embodiments, the harvested AAV has a titer between about $2\times10^{10}$ vg/mL and about $8\times10^{11}$ vg/mL. In embodiments, the harvested AAV has a titer between about $2\times10^{10}$ vg/mL and about $7\times10^{11}$ vg/mL. In embodiments, the harvested AAV has a titer between about $2\times10^{10}$ vg/mL and about $6\times10^{11}$ vg/mL. In embodiments, the harvested AAV has a titer between about $2\times10^{10}$ vg/mL and about $5\times10^{11}$ vg/mL. In embodiments, the harvested AAV has a titer between about $2\times10^{10}$ vg/mL and about $4\times10^{11}$ vg/mL. In embodiments, the harvested AAV has a titer between about $2\times10^{10}$ vg/mL and about $3\times10^{11}$ vg/mL. In embodiments, the harvested AAV has a titer between about $2\times10^{10}$ vg/mL and about $2\times10^{11}$ vg/mL. In embodiments, the harvested AAV has a titer between about $2\times10^{10}$ vg/mL and about $1\times10^{11}$ vg/mL. The titer may be any value or subrange within the recited ranges, including endpoints.

The cells may be cultured in any volume of cell culture medium that supports growth of the cells and production of AAV. In embodiments, the cells are cultured in a volume of about 15 milliliters (mL) to about 200 liters (L). In embodiments, the cells are cultured in a volume of about 30 mL to about 200 L. In embodiments, the cells are cultured in a volume of about 50 mL to about 200 L. In embodiments, the cells are cultured in a volume of about 100 mL to about 200 L. In embodiments, the cells are cultured in a volume of about 500 mL to about 200 L. In embodiments, the cells are cultured in a volume of about 1 L to about 200 L. In embodiments, the cells are cultured in a volume of about 10 L to about 200 L. In embodiments, the cells are cultured in a volume of about 15 mL to about 100 L. In embodiments, the cells are cultured in a volume of about 15 mL to about 50 L. In embodiments, the cells are cultured in a volume of about 15 mL to about 20 L. In embodiments, the cells are cultured in a volume of about 15 mL to about 5 L. In embodiments, the cells are cultured in a volume of about 15 mL to about 1 L. In embodiments, the cells are cultured in a volume of about 15 mL to about 500 mL. In embodiments, the cells are cultured in a volume of about 500 mL to about 10 L. In embodiments, the cells are cultured in a volume of about 1 L to about 10 L. The culture volume may be any value or subrange within the recited ranges, including endpoints.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

EXAMPLES

One skilled in the art would understand that descriptions of making and using the particles described herein is for the sole purpose of illustration, and that the present disclosure is not limited by this illustration.

Example 1. Effect of Culture Conditions on Viral Titer

Adherent HEK293T cells and HEK293F cells were cultured in an incubator at 37° C., 8% $CO_2$ and 80% humidity. Cells were transfected with AAV transfer vector, pAAV-RC and pAAV-Helper at a density of about $4\times10^6$ cells/mL in a 6-well plate using PEI (HEK293T) or System 1 (HEK293F) under one of the following conditions: Prot-1 (enhancer 1 and supplement 1), Prot-2 (supplement 1, no enhancer), Prot-3 (enhancer 1, no supplement). System 1 includes medium that supports HEK293 cell growth and proliferation (LV-MAX™ Production Medium, GIBCO™, Thermo Fisher Scientific, catalog no. A3583401), LV-MAX™ transfection reagent, LV-MAX™ supplement, and LV-MAX™ enhancer (GIBCO™, Thermo Fisher Scientific, catalog no. A35348). AAV were extracted by adding 200 μL of 5×AAV lysis buffer to 800 μL transfected cell culture, mixing well and incubating at room temperature for 30 min. After incubation, the tube was inverted to completely lyse cells, then spun at maximum speed in a tabletop centrifuge for 10 min. Supernatants containing crude AAV was collected.

AAV were titered by qPCR with primers and probe to ITR2. Briefly, extracts were treated with DNase and proteinase K. Extracts were diluted 1:50 in water, and qPCR performed and compared to a standard curve (digested AAV plasmid).

Results are provided in FIG. 1. For HEK293F cells, System 1 without LV-MAX™ supplement resulted in the highest AAV titer.

Example 2. Effect of Culture Medium on Viral Titer

HEK293F cells were established in four different types of commercially available media that support HEK293F cells in suspension culture. Cells were frozen in their adapted media, and thawed prior to use. Thawed cells were transfected with AAV transfer vector (pAAV-GFP). AAV transfer vector, pAAV-RC2 and pAAV-Helper were complexed with AAV transfection reagent at 1:4 w/w ratio, and with transfection booster at 2:1 (v/w) ratio in Opti-MEM complex solution buffer, then incubated for 10 minutes at room temperature. After incubation, DNA/transfection reagent complex mixture was directly added to prepared cell culture. AAV2 production occurred at cell passage 6 for all four cell systems/media types.

Figure 2:
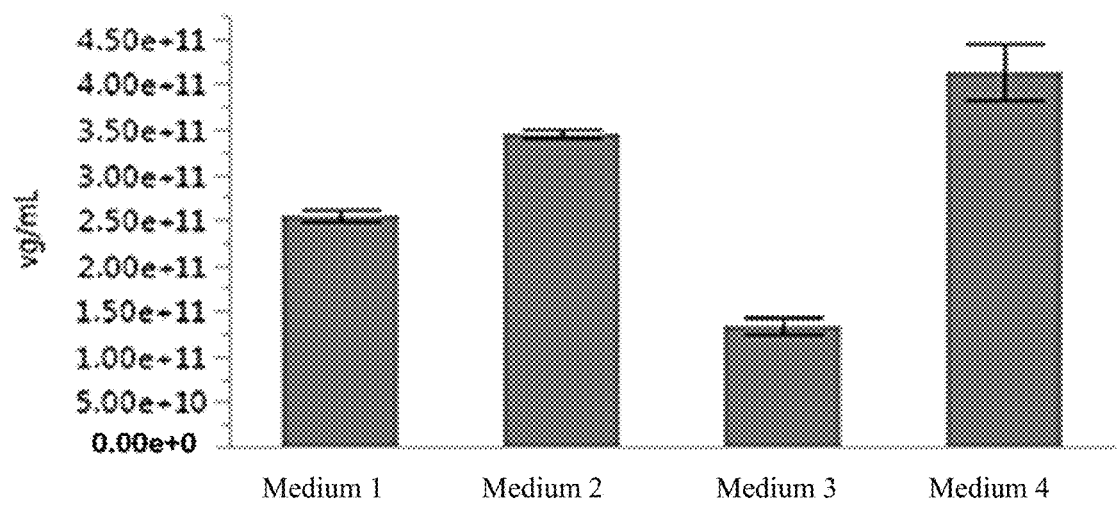
FIG. 2 shows AAV2 production comparison for HEK293F cells adapted in four different types of culture media.

FIG. 2 shows that HEK293F cells adapted in medium 4 produced more AAV2 than the other media tested.

Example 3. Characteristics of Medium 4-Adapted Cells

Figure 3:
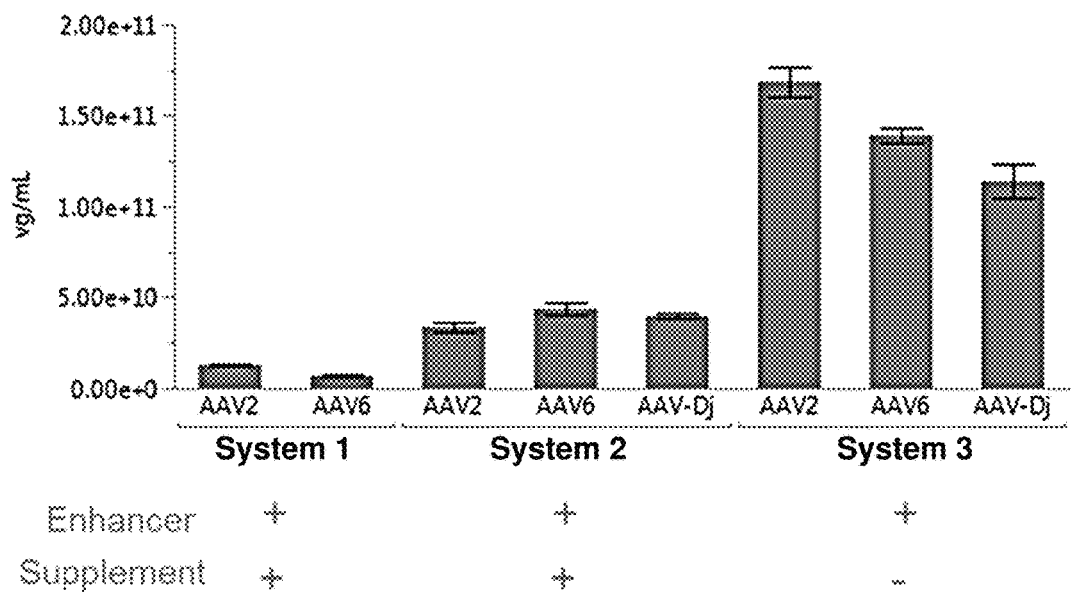
FIG. 3 shows a comparison of three different systems for AAV production. HEK293 cells adapted to medium 4 were tested with System 1, System 2, and System 3, as detailed in the Examples.

To determine the optimal conditions for transfection of HEK293F cells that were established in medium 4, the effect of different transfection reagents was evaluated. Cells were transfected with AAV2, AAV6, or AAV-Dj using: System 1, HEK293F cells with LV-MAX Transfection Reagent, Enhancer and Supplement (see Example 1); System 2: HEK293F cells using a different transfection reagent (Transfection Reagent 2) with LV-MAX Enhancer and Supplement; and System 3: medium 4-adapted HEK293 cells with Transfection Reagent 2 and LV-MAX Enhancer, without Supplement. Viral titers in medium 4-adapted HEK293 cells were highest using System 3 for all AAV serotypes (FIG. 3). Transfection Reagent 2 is a cationic lipid transfection reagent including a peptide-containing transfection booster (as described herein).

Example 4. Clone 45 Cells

Figure 4A:
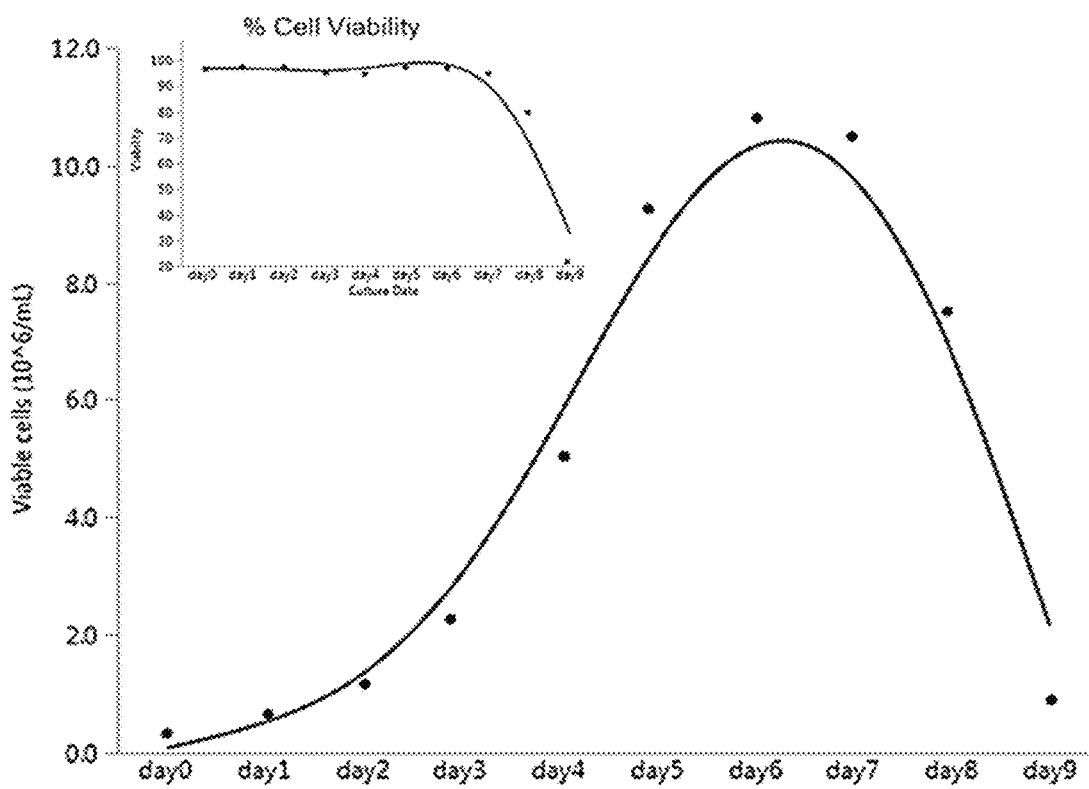
FIGS. 4A-4B show a growth characteristics for clonal HEK293 cells adapted to medium 4 (Clone 45). Culture medium supported Clone 45 cells growing at high density (~11×10$^6$ cells/mL) with high cell viability (FIG. 4A). Cells have very limited clumping at high density, as shown in FIG. 4B.
Figure 4B:
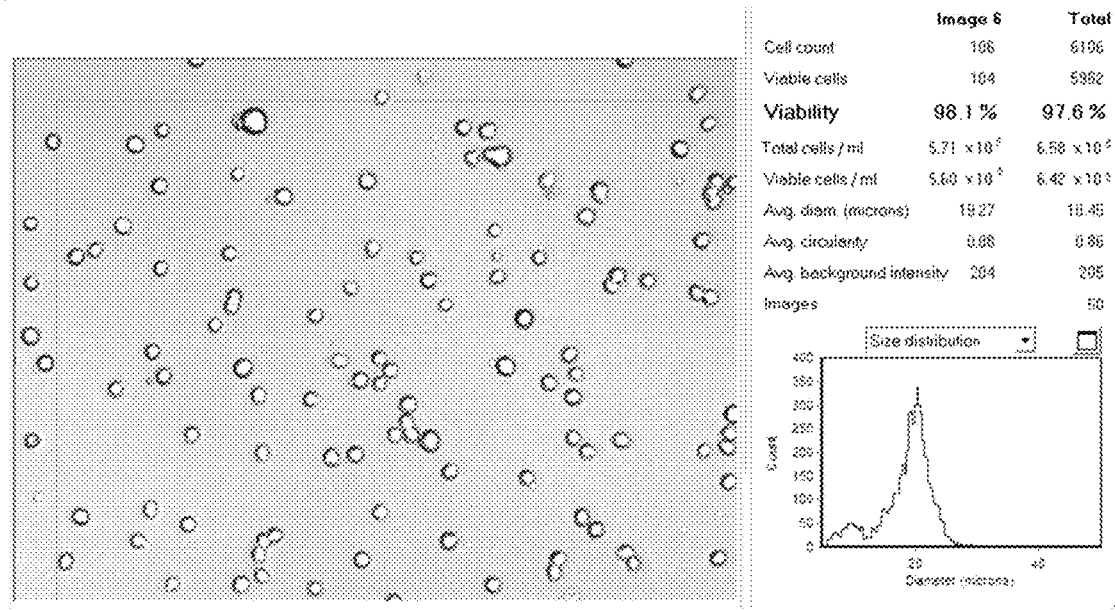
Figure 5A:
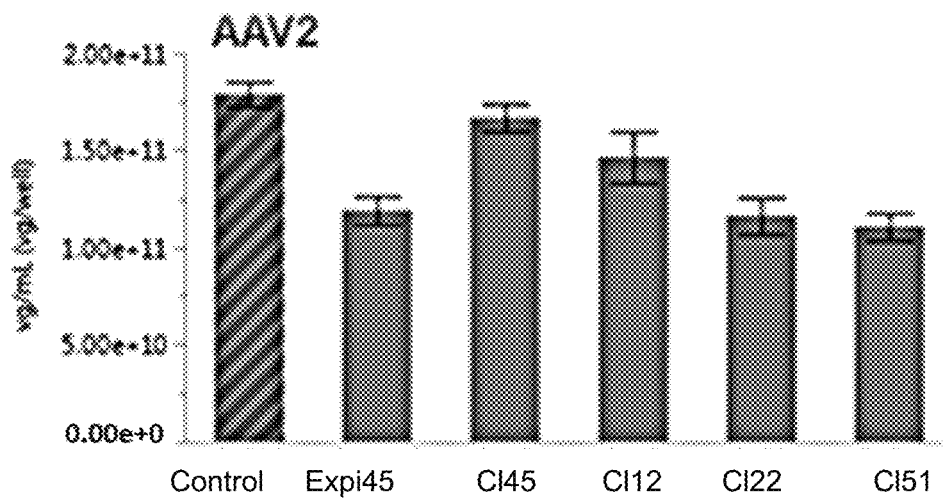
FIGS. 5A-5E show production of different AAV serotypes in clonal HEK293 cells. Control: Parental HEK293 cells in medium 4; Expi45: Clone 45 in Expi293 medium; Cl45, Cl12, Cl22 and Cl51: indicated HEK293 clone in medium 4.
Figure 5B:
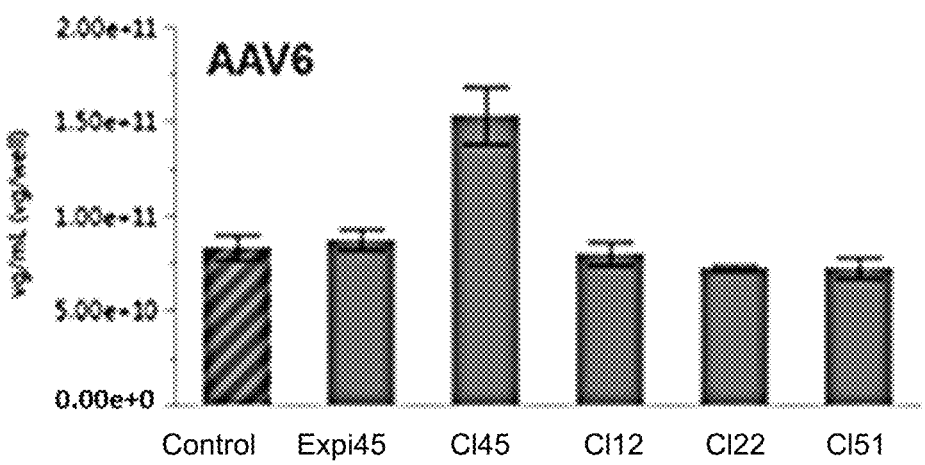
Figure 5C:
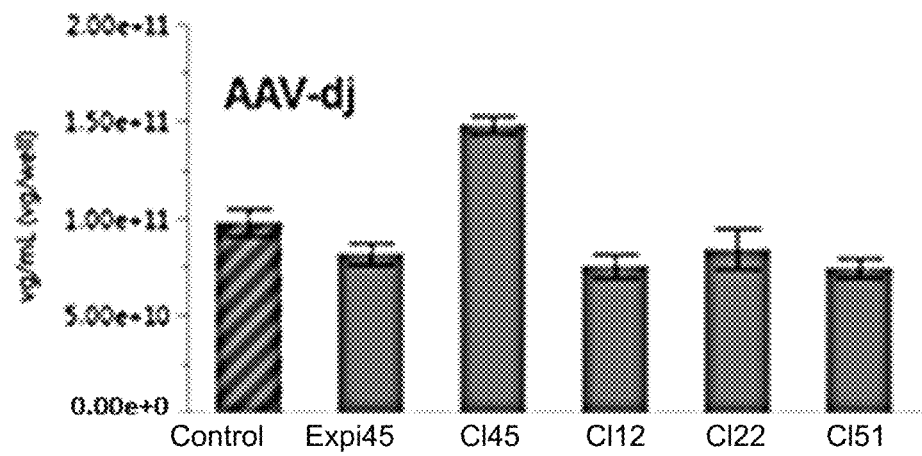
Figure 5D:
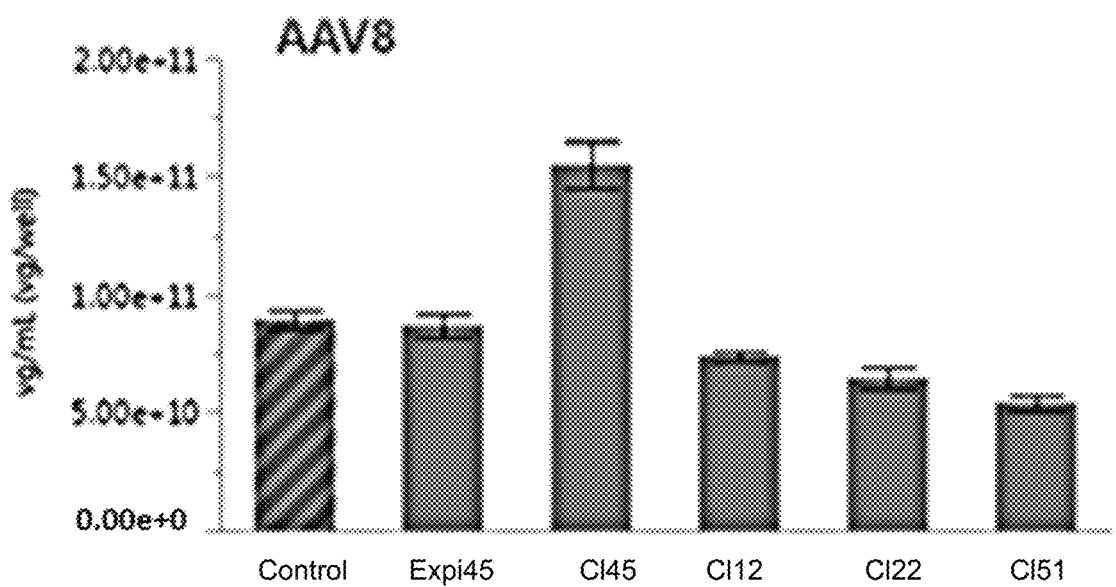
Figure 5E:
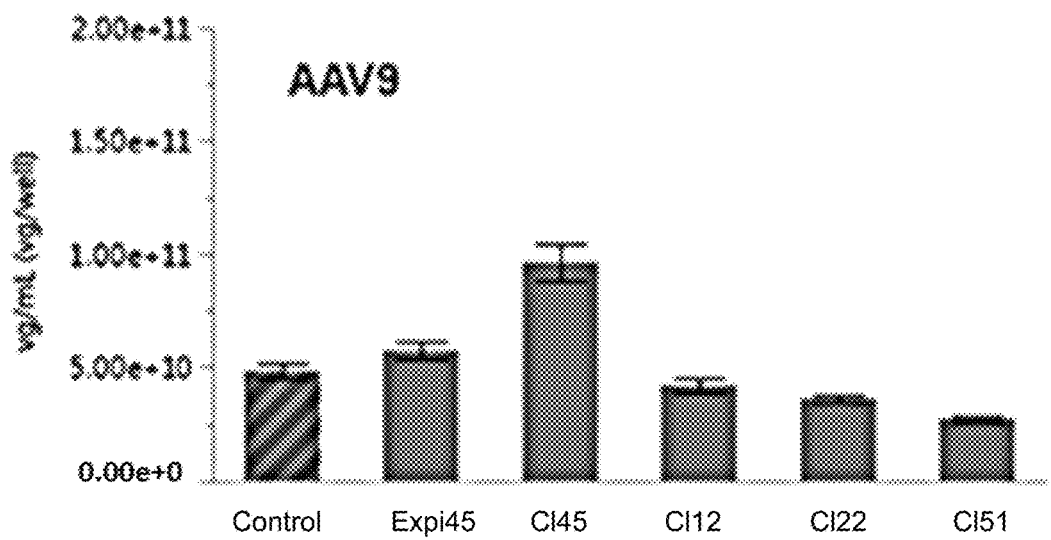

Growth characteristics of a clonal population of the medium 4-adapted HEK293 cells (clone 45) were evaluated. Clone 45 cells were split at passage 5 to a cell density of $0.3\times10^6$ viable cells/mL in 250 mL shake flasks in medium 4. Cell density and cell viability were collected each day for 9 days. Growth curve is shown in FIG. 4A (inset: percent cell viability). Medium 4 supported high cell densities of up to about $11\times10^6$ cells/mL and the clone 45 cells in high density culture demonstrated high cell viability. As shown in FIG. 4B, clone 45 cells exhibit very little clumping, even at high density.

The ability of clone 45 cells and three other medium-4 adapted clonal lines to produce acceptable titers of different AAV serotypes in medium 4 was evaluated. Clone 45 cells were grown in EXPI293™ expression medium (Expi45; GIBCO™ Thermo Fisher Scientific, catalog no. A1435101) or medium 4 (Cl45) and transfected with AAV2, AAV6, AAV-dj, AAV8, or AAV9 vectors caring a transgene encoding GFP. Similarly, medium 4-adapted clonal lines clone 12 (Cl12), clone 22 (Cl22), and clone 51 (Cl51) were grown in medium 4 and transfected with the vectors of the 5 AAV serotypes. Transfection was performed using Transfection Reagent 2 as described above. Production in clone 45 cells was compared to parental cell line (parental HEK293, Control), or the three other medium 4-adapted clonal lines. The resultant AAV titers were determined using qPCR with AAV-GFP primers and probe as described elsewhere herein. Clone 45 cells grown in medium 4 resulted in high viral titers, between about $1\times10^{11}$ vg/mL and about $2\times10^{11}$ vg/mL, for each serotype (FIGS. 5A-5E).

Figure 6:
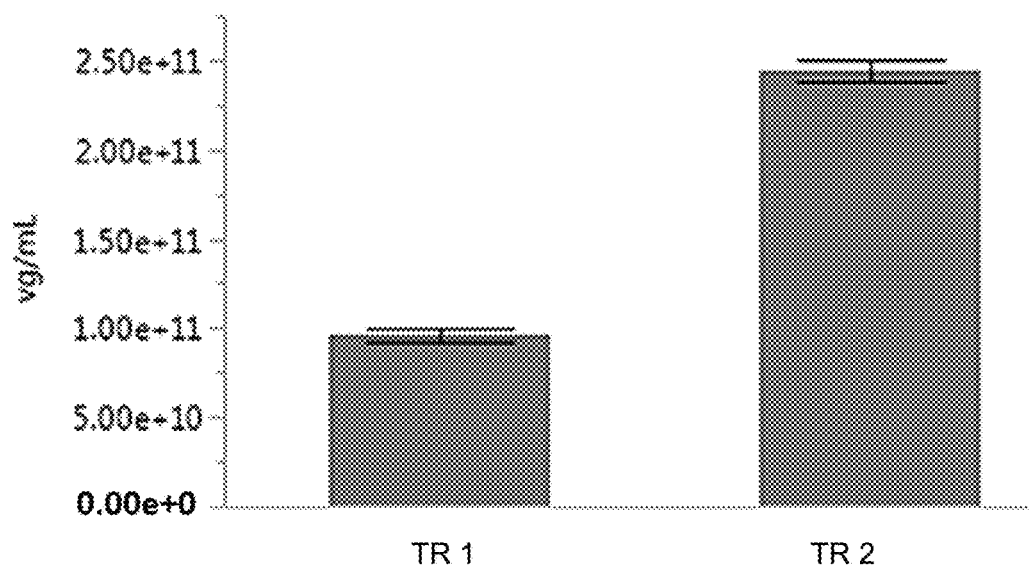
FIG. 6 shows a comparison of transfection reagents. Transfection reagent 1 (TR1) was compared with Transfection reagent 2 (TR2) for AAV2 production.

The effect of different transfection reagents on viral production by clone 45 cells was also evaluated. Cells were transfected with LV-MAX™ transfection reagent (TR1) or transfection reagent 2 (TR2). Transfection reagent 2-mediated plasmid delivery produced more AAV virus than LV-MAX™ transfection reagent under these conditions (FIG. 6).

Example 5. Addition of Enhancer Improves Virus Production

Figure 7:
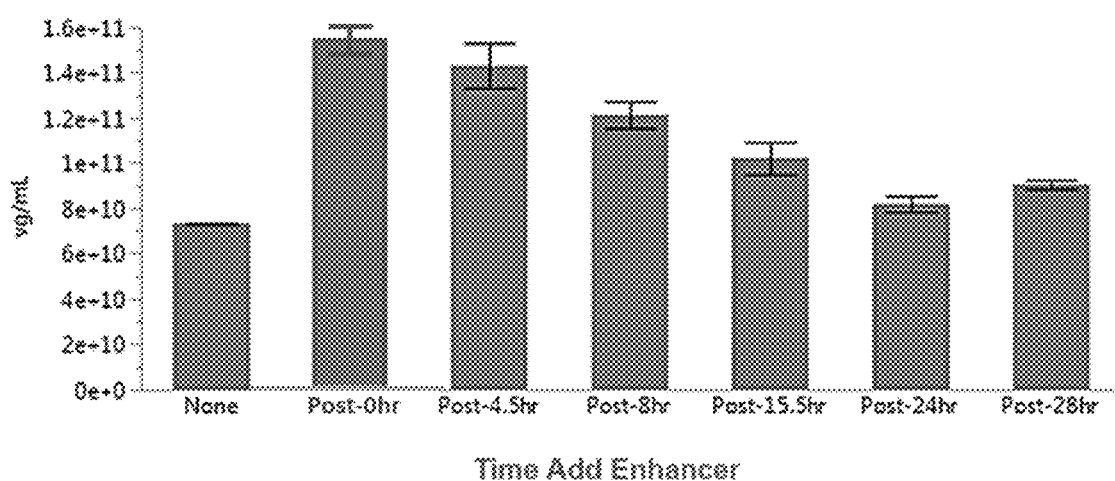
FIG. 7 shows the effect of timing of Enhancer addition on viral titer in the AAV production system.

Clone 45 cells in medium 4 were transfected with AAV plasmid using transfection reagent 2, with or without addition of enhancer at 0, 4.5, 8, 15.5, 24, or 28 hours after transfection. Addition of the enhancer, in particular between 0 and 15.5 hours after transfection, increases AAV production (FIG. 7). The enhancer contains an HDAC inhibitor, sodium propionate, sodium butyrate, and caffeine.

Example 6. Screening of Lysis Buffer Reagents

Using a JMP® Design of Experiments (DOE) platform, a screening experiment was designed using four core chemicals as potential detergents in the lysis buffer: Triton-alter, CHAPSO, Big CHAP, and NDSB-201.

The DOE platform allowed investigators to vary multiple parameters simultaneously, instead of varying each of the parameters individually and then considering each optimized parameter for an overall optimized formulation. When second-order effects between parameters can impact results, the DOE platform, varying all candidate parameters simultaneously, allows for a more efficient and accurate result. Experiments using the DOE platform also require fewer runs and are more economical than traditional experimental approaches. See Kauffman et al., Optimization of Lipid Nanoparticle Formulations for mRNA Delivery in Vivo with Fractional Factorial and Definitive Screening Designs, *Nano Letters* 15:7300-7306 (2015) and supplemental materials for a theoretical discussion on DOE platforms.

Triton-alter, CHAPSO, Big CHAP, and NDSB-201 were evaluated at different concentrations, as indicated in Table 1. Percentages are provided as weight per volume (w/v).

TABLE 1

Amount of each detergent used.

| Run# | Triton-alter | CHAPSO | Big CHAP | NDSB-201 (mM) |
|---|---|---|---|---|
| R1 | 0.00% | 0.00% | 0.00% | 100 |
| R2 | 0.00% | 0.00% | 0.50% | 0 |
| R3 | 0.00% | 0.25% | 0.00% | 0 |
| R4 | 0.00% | 0.25% | 0.25% | 200 |
| R5 | 0.00% | 0.50% | 0.50% | 100 |
| R6 | 0.15% | 0.00% | 0.00% | 0 |
| R7 | 0.15% | 0.00% | 0.50% | 200 |
| R8 | 0.15% | 0.25% | 0.35% | 100 |
| R9 | 0.15% | 0.50% | 0.00% | 200 |
| R10 | 0.15% | 0.50% | 0.25% | 0 |
| R11 | 0.30% | 0.00% | 0.25% | 100 |
| R12 | 0.30% | 0.25% | 0.00% | 200 |
| R13 | 0.30% | 0.25% | 0.50% | 0 |
| R14 | 0.30% | 0.50% | 0.00% | 100 |
| R15 | 0.30% | 0.50% | 0.50% | 200 |

Figure 8:
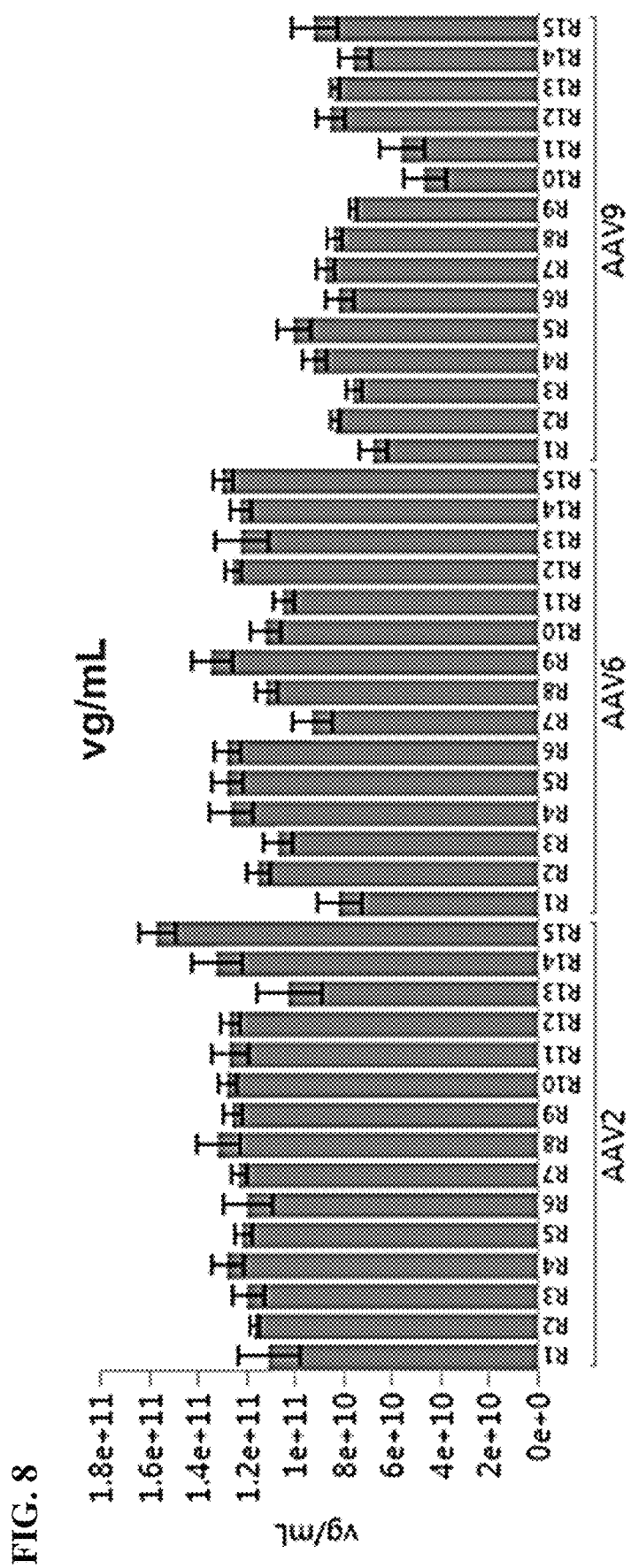
FIG. 8 shows the effect of various detergents in the AAV lysis buffer on viral titer.

Jmp software was used to analyze results to determine detergent influence during the cell lysing process. The results are provided in FIG. 8 for three different AAV serotypes.

Figure 9:
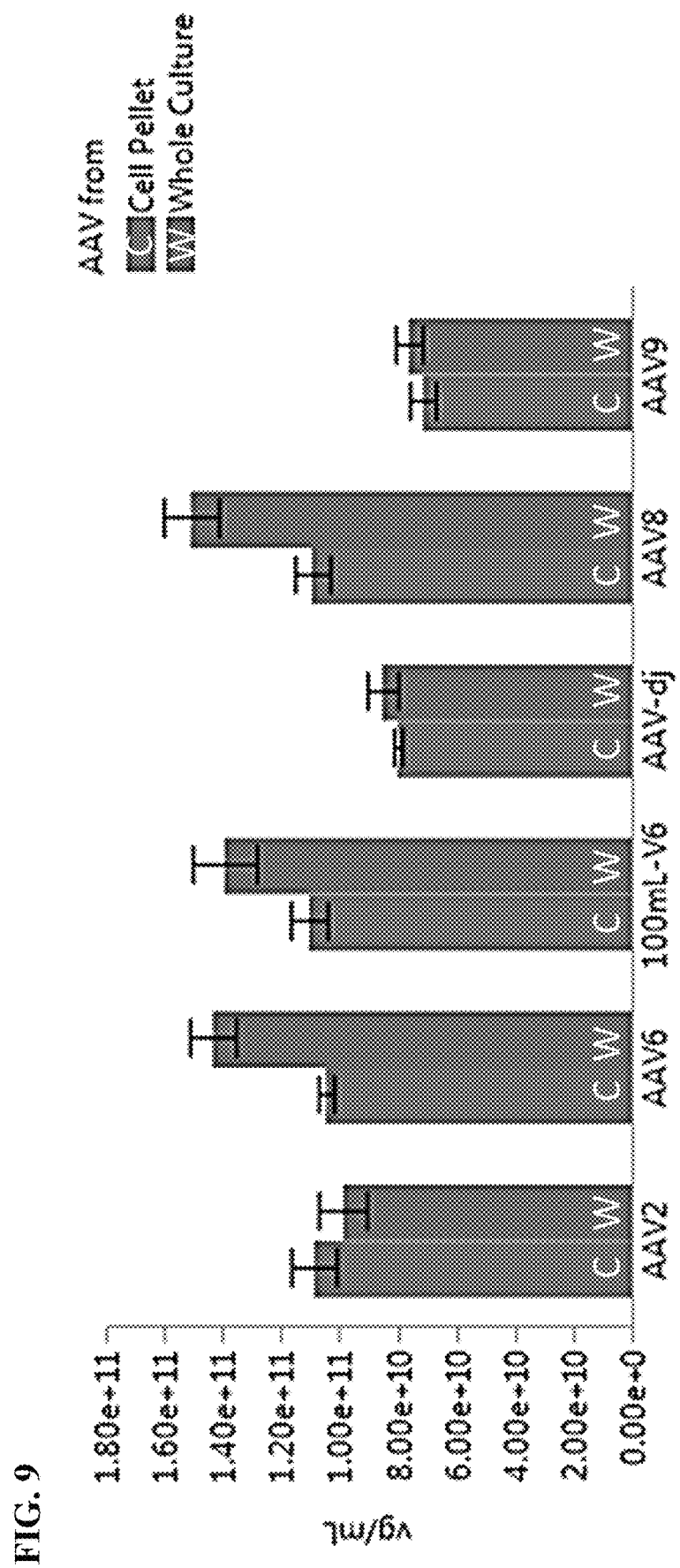
FIG. 9 shows extract AAV titer from cell pellets versus the whole transfected cell culture for different AAV serotypes.

The lysis buffer was also tested on AAV extracts from transfected cell culture versus cell pellets. Clone 45 cells were transfected with AAV plasmids using transfection reagent 2 and the enhancer. AAV were extracted 70-72 hours post-transfection by adding 1×lysis buffer to the cell pellet, or 5×lysis buffer to the whole cell culture (transfected cells and culture media). Resulting AAV titers are provided in FIG. 9.

Example 7. A First AAV Production Protocol

The following guidelines for suspension culture of AAV production cells are followed. The cells are grown according to standard AAV suspension cell culture protocols. The cells are subcultured when they reached a density of approximately $3 \times 10^6$ to $6.5 \times 10^6$ viable cells/mL, typically every 3-4 days. The cells are split to $0.3 \times 10^6$ to $0.6 \times 10^6$ cells, after about 3 or 4 days of culture. The cell growth is monitored by counting the cells daily at approximately the same time every day. During cell culture, an orbital shaker (19 mm orbital diameter) is used at about 125 rpm for 125 mL to 1 L shaker flasks. The incubator is set to about 37° C., about 8% $CO_2$, and about 75-80% humidity.

Reagents and Materials:
 125 mL, 250 mL, 1 L polycarbonate, disposable, sterile, vent-up and no baffled Erlenmeyer shaker flasks
 50 mL sterile conical tubes
 Opti-MEM I Medium
 Clone 45 Cells
 AAV293 Culture Medium
 AAV Transfection Reagent and Transfection Booster
 AAV Enhancer
 5×AAV Lysis buffer If cells are split on Friday morning to a cell count of $0.55 \times 10^6$ cells/mL, for example, they may be cultured for 3 days in 1 L flask at about 300 mL culture medium. On Monday morning, for example, the cells are prepared by counting the cells, and a cell density of around $4.0 \times 10^6$ cells/mL may be expected. The cells may be diluted in fresh warmed culture medium to about $3.0 \times 10^6$ cells/mL and cultured for another 24 hours (approximate).

The transfection may be carried out on Tuesday, for example. The cells may be counted and diluted to between about $2.5 \times 10^6$ cells/mL and about $4 \times 10^6$ cells/mL in 30 mL cell culture medium in 125 mL flasks. Table 2 provides amounts of each plasmid at various ratios. Table 3 provides additional transfection guidelines.

TABLE 2

Different DNA Ratio Preparation

| DNA Ratio# | Plasmid | DNA Ratio (w/w) | Total DNA/ml | Each plasmid ug/ml | Each plasmid ug for 1 × 30 ml | Each plasmid ug for 3 × 30 ml |
|---|---|---|---|---|---|---|
| #1 | pAAV-GFP | 1 | 1.5 ug | 0.5 | 15 | 45 |
|  | pRC | 1 |  | 0.5 | 15 | 45 |
|  | pHelper | 1 |  | 0.5 | 15 | 45 |
| #2 | pAAV-GFP | 1 | 1.5 ug | 0.25 | 7.5 | 22.5 |
|  | pRC | 3 |  | 0.75 | 22.5 | 67.5 |
|  | pHelper | 2 |  | 0.5 | 15 | 45.0 |
| #3 | pAAV-GFP | 1 | 1.5 ug | 0.214 | 6.4 | 19.2 |
|  | pRC | 3 |  | 0.64 | 19.3 | 57.9 |
|  | pHelper | 3 |  | 0.64 | 19.3 | 57.9 |

TABLE 3

DNA/Transfection Reagent Complexation Preparation

| DNA/tfx reagent Complexation Steps | Tubes | DNA/tfxR Complex | AAV Production Volume | | |
|---|---|---|---|---|---|
|  |  |  | 1 mL | 30 mL | 3 × 30 mL |
| Step-1 | Tube-1 (diluted DNA + TfxR Booster) | Opti-MEM I | 0.5 mL | 1.5 mL | 4.5 mL |
|  |  | Plasmid DNA (Ratio-1 or 2 or 3) | 1.5 ug | 45 ug | 135 ug |
|  |  | DNA; Tfx Booster 1 ug:2 ul | 3 ul | 90 ul | 270 ul |
|  |  | Briefly vortex | | | |

TABLE 3-continued

| DNA/Transfection Reagent Complexation Preparation | | | | | |
|---|---|---|---|---|---|
| DNA/tfx reagent | | DNA/tfxR | AAV Production Volume | | |
| Complexation Steps | Tubes | Complex | 1 mL | 30 mL | 3 × 30 mL |
| Step-2 | Tube-2 (diluted TfxR) | Opti-MEM I | 0.5 mL | 1.5 mL | 4.5 mL |
| | | AAV TfxR | 6 ul | 180 ul | 540 ul |
| | | Briefly Vortex and incubate at RT for 1 minute | | | |
| Step-3 | Add Tube-2 solution to Tube-1 => Briefly vortex | | | | |
| Step-4 | Incubate the Step-3 mixture at RT for 10 mins | | | | |
| Step-5 | add ~3.2 ml of DNA/AAV TfxR complex to one of 3 flasks in a cell group | | | | |

The DNA/transfection reagent is prepared as follows. Two tubes are labeled Tube-1 and Tube-2. In Tube-1: 4.5 mL of OPTI-MEM™ I medium and 135 µg of DNA (in a ratio as indicated in Table 2) are mixed and 270 µL transfection booster added. In Tube-2: 4.5 mL of OPTI-MEM™ I medium is mixed with 540 µL transfection reagent and incubated at room temperature for 1 minute. Tube-1 and Tube-2 are combined by adding Tube-2 solution to Tube-1 with mixing, then incubated at room temperature for 10 minutes. Approximately 3.2 mL of the DNA/AAV transfection reagent complex is added to each flask of cells. AAV enhancer is added at the time of transfection at 1% v/v per flask.

AAVs are harvested 70-72 hours after transfection, for example Friday morning. Alternatively, transfected cell cultures may be stored at −80° C. (800 µL of sample should be stored separately at −80° C. for titering). 5×AAV lysis buffer is added at a 1:5 dilution (200 µL lysis buffer per 800 µL transfected cell culture sample), pipetted up and down and vortexed to mix. Samples are incubated for about 30 minutes, then inverted by hand 25-30 times. Cells are fully lysed once the culture solution is clear and a chunk of cell debris is observed.

Lysed cells are spun at 4° C. for 10 minutes (maximum speed in benchtop centrifuge). Supernatant containing crude AAV is transferred to a new tube and stored at 4° C. Samples are titered, for example by qPCR.

Example 8. Measurement of AAV Titer from the Production in Example 7

Supernatant from Example 7 is mixed well and 100 µL of crude AAV samples is aliquoted to each of 2 wells of a 96-well round bottom plate with lid. Samples are digested with DNase I by adding 2 µL crude AAV sample to 2 µL 10×Dnase I buffer, and 137 units DNase I, in a total volume of 20 µL; and incubating at 37° C. for 60 min, 95° C. for 20 min, and then 4° C.

DNase-treated samples are digested with proteinase K by adding 19 µL 2×PK buffer and 20 µg proteinase K to each sample and incubating at 60° C. for 60 min, 95° C. for 10 min, and then 4° C.

After proteinase K digestion, samples are diluted 1:50 in water. Quantitative PCR (qPCR) is run using primers and a labeled probe specific for the AAV-GFP gene.

A standard curve is generated using linearized AAV transfer plasmid. For pAAV-GFP, the plasmid is linearized by digestion with HindIII or BamHI, then DNA concentration determined. Linearization may be determined by loading cut and uncut plasmid onto a 0.8% agarose gel and visualizing the resulting bands after electrophoresis. Uncut plasmid should appear as a smear, cut plasmid should be one large band at ~5 kb.

QPCR is performed in a 384-well qPCR sample plate using 2×EXPRESS qPCR Supermix, with premixed ROX (Thermo Fisher Scientific) according to manufacturer's instructions. Briefly, 3 µL diluted sample (or standard curve) is combined with 7.5 µL 2× Supermix, 0.11 µL AAV-GFP probe (FAM/TAMRA), 1.13 µL GFP-specific primers (mixed forward and reverse primers at 10 and 3.26 µL water. Samples are run in a qPCR machine using the following cycling program: 50° C. for 2 minutes (UDG incubation); 95° C. for 2 minutes; 40 cycles of: 95° C. for 15 seconds, 60° C. for 1 minute.

Example 9. AAV-GFP Viral Infectious Test Protocol

AAV may be tested for the ability to infect target cells (e.g., Ht1080 or HEK293). Cells are seeded in a 96-well plate at a density of 7000 cells/well in 100 µL culture medium about 4 hours before infection.

Cells are infected by adding 1 µL crude AAV preparation to each well. Cells are incubated for approximately 3 days. For AAV that contain an expressible green fluorescent protein (GFP) gene, flow cytometry is run to measure percentage of cells expressing GFP.

Example 10. AAV Production System Comparisons

Figure 10A:
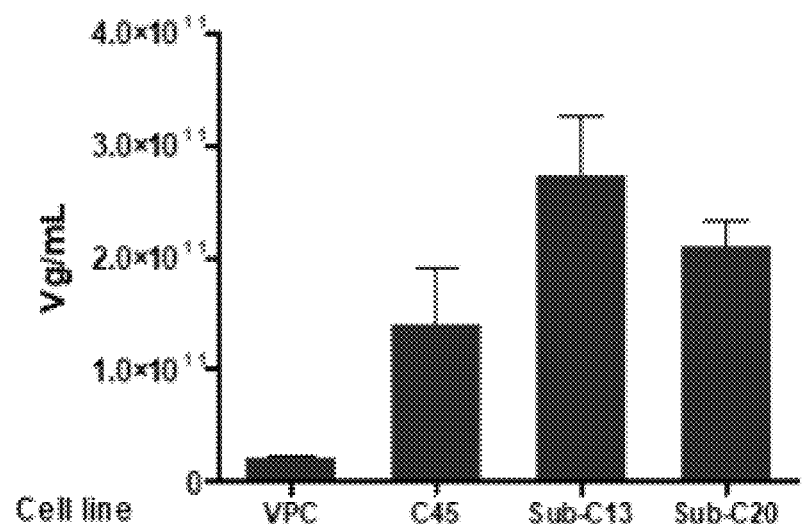
FIGS. 10A-10B show a comparison of clone 45, subclonal lines C13 and C20, and LV293 cells (VPC) in AAV production (FIG. 10A) and cell viability (FIG. 10B) following transfection.
Figure 10B:
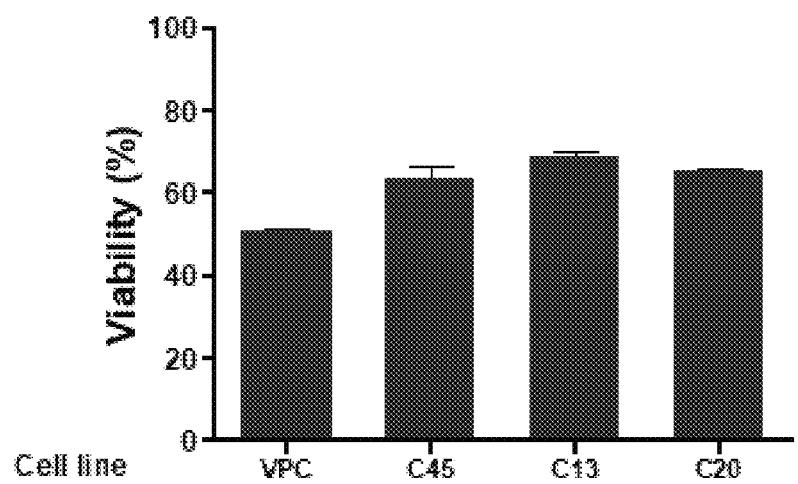

AAV vector production from clone 45 and from two sub-clonal lines derived from clone 45 were compared to that from an HEK293F derivative LV293 (LV-MAX Viral Production Cells (VPC), Thermo Fisher Scientific). The cells were grown according to culture protocols described above and were transfected with pAAV-GFP, pAAV-Helper, and pAAV-RC for AAV8. Transfection was performed with Transfection Reagent 2 with Transfection Booster as described above. About 72 hours after transfection, AAV titer (via qPCR for GFP (Example 8)) and cell viability of the cultures were determined. Clone 45 and the sub-clonal lines C13 and C20 produced significantly higher AAV8 titers (between about $1.5 \times 10^{11}$ to about $2.5 \times 10^{11}$ vg/mL) as compared to the same system with LV293 (VPC, FIG. 10A). In addition, AAV producing cultures with clone 45, C13 and C20 had notably higher cell viability than the culture with LV293 (VPC, FIG. 10B).

Figure 11A:
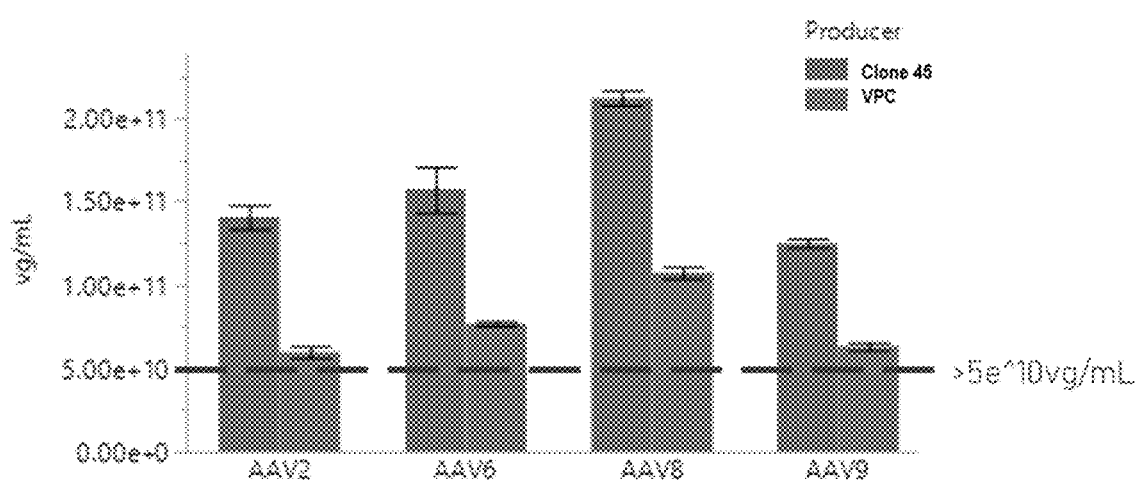
FIGS. 11A-11B show a comparison of clone 45 and LV293 cells (VPC) in AAV production.
Figure 11B:
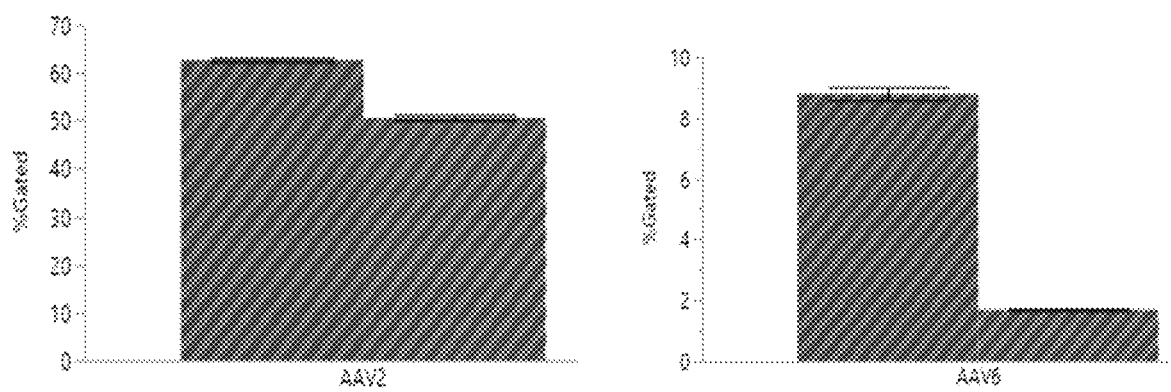

Vector production across various AAV serotypes in clone 45 cells was compared to that in LV293 (VPC) cells. Cells were grown according to suspension cell culture protocols for AAV as described above and the cells were diluted in 30 ml cell culture medium-4 in 125 mL flasks (clone 45 at $3 \times 10^6$ cells/mL and LV293 at $2.5 \times 10^6$ cells/mL). The cells were transfected with pAAV-GFP, pAAV-Helper, and pAAV-RC for AAV2, AAV6, AAV8 and AAV9. Transfection was performed with Transfection Reagent 2 with Transfection Booster as described above. AAVs from the cultures were harvested about 72 hours after transfection. The AAV titers were determined via the qPCR for GFP method and via the infectious test protocol (Example 9). Exemplary results are shown in FIG. 11. The AAV production system with clone 45 as the producer cell resulted in significantly higher viral titers (between about $1.3 \times 10^{11}$ to about $2.15 \times 10^{11}$ vg/mL) across the serotypes as compared to the same system with LV293 (VPC, FIG. 11A). As shown in FIG. 11B, the AAV production system with clone 45 also resulted in AAV2 and AAV6 with greater infectivity than the LV293 VPC cells.

AAV vector production with the AAV vector production system provided herein was compared to two polyethylenimine (PEI)-based production systems. The PEI-based transfection systems were performed according manufacturers' instructions and known methods. In one analysis, cells were transfected with pAAV-GFP, pAAV-Helper, and pAAV-RC for AAV6: (1) LV293 cells were transfected using PEIpro™ (Polyplus transfection) without enhancer and (2) clone 45 cells were transfected with Transfection Reagent 2 with Transfection Booster and AAV production enhancer as described above. After the culture period, AAVs were harvested and titers determined via the qPCR for GFP method and via the infectious test protocol. Exemplary results are shown in FIG. 12. The AAV production system provided herein resulted in significantly higher AAV6 titer (FIG. 12A) and infectivity (FIG. 12B) than the LV293 with PEIpro system.

Figure 13B:
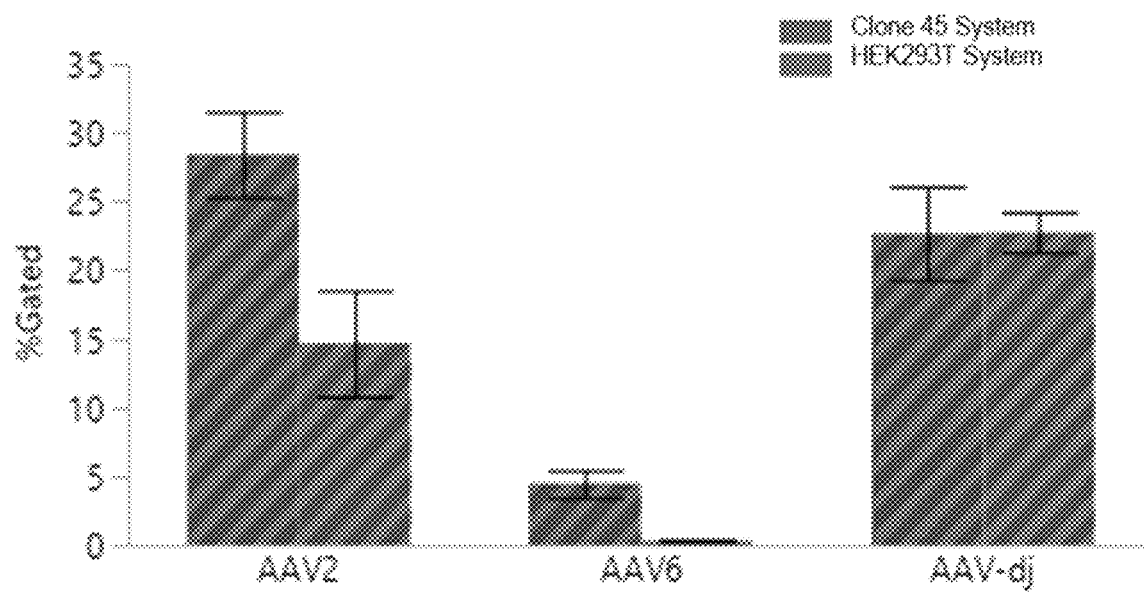

In another analysis, vector production across various AAV serotypes was compared using: (1) HEK293T adherent cells with PEI-MAX transfection reagent (Polysciences, Inc.) and clone 45 cells with Transfection Reagent 2 and Transfection Booster as described above. The cells were transfected with pAAV-GFP, pAAV-Helper, and pAAV-RC for AAV2, AAV6, AAV8, AAV9, and AAV-dj. After the culture period, AAVs were harvested and titers determined via the qPCR for GFP method and via the infectious test protocol. Exemplary results are shown in FIGS. 13A-B. The AAV production system provided herein resulted in significantly higher AAV titer across 4 of the 5 serotypes tested than the HEK293T with PEI-MAX system (FIG. 13A). As shown in FIG. 13B, the AAV production system provided herein also resulted in AAV2 and AAV6 with greater infectivity than the with PEI-MAX system.

Example 11. Post-Harvest Processing

Figure 14:
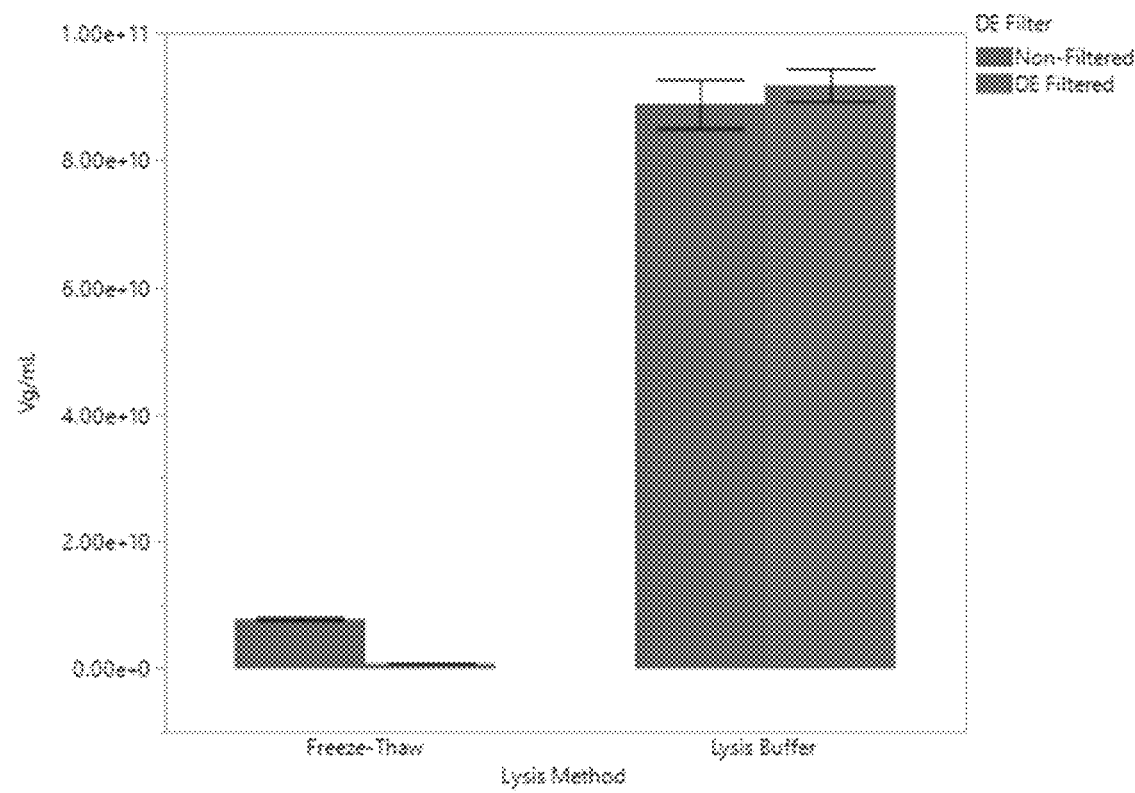
FIG. 14 shows AAV titers in crude lysate before and after diatomaceous earth filtration.

Following transfection, virus production and cell lysis, crude AAV lysate was filtered using diatomaceous earth prior to downstream processing. Two samples from the same AAV culture were lysed with either a freeze-thaw method (without lysis buffer) or with addition of 10×AAV lysis buffer and 30 minute incubation (as described above) to form a crude AAV lysate. Immediately following lysis, diatomaceous earth (DE) was mixed with the crude AAV lysate and the mixture was passed through a 2 micron filter. Various amounts of DE per mL of lysate were tested including 0.5 g DE:30 mL lysate and 1 g DE:100 mL lysate. Samples were taken from each lysate before and after DE filtration to determine recovery of AAV following the filtration step. AAV titers from the samples were determined using GFP qPCR and exemplary results are shown in FIG. 14. Forming a crude lysate with the AAV lysis buffer method resulted in high recovery of AAV titer during DE filtration whereas the freeze-thaw cell lysis method resulted in substantially lower recovery. As shown in FIG. 14, for example, about 100% titer recovery was obtained with lysis buffer compared with about 10% recovery with freeze-thaw. The single DE filtration step reduced the number of filters needed and greatly reduced the filtration and processing time of AAV lysate prior to downstream processing, such as nuclease treatment and purification processes.

What is claimed is:
1. An adeno-associated virus (AAV) production system, comprising:
(a) mammalian cells adapted for suspension culture;
(b) an AAV transfer vector;
(c) one or more packaging plasmids;
(d) an enhancer comprising one or more histone deacetylase (HDAC) inhibitor; and
(e) cell culture media that supports growth and expansion of the mammalian cells.
2. The AAV production system of claim 1, further comprising a transfection reagent.
3. The AAV production system of claim 2, wherein the transfection reagent is a cationic lipid or polymer-based transfection agent.
4. The AAV production system of claim 2, wherein the transfection reagent further comprises a peptide.
5. The AAV production system of claim 1, further comprising a transfection booster.
6. The AAV production system of claim 5, wherein the transfection booster comprises a peptide.
7. The AAV production system of claim 1, further comprising a lysis buffer.
8. The AAV production system of claim 7, wherein the lysis buffer comprises at least one surfactant selected from: Triton-100, Triton-alter, NP-40, poloxamer 188, and NDSB-201.
9. The AAV production system of claim 7, wherein the lysis buffer comprises at least one of: Tris-HCl, sodium citrate, sodium chloride, citric acid, EDTA, tri-potassium EDTA, sodium hydroxide, and sodium dihydrogen phosphate.
10. The AAV production system of claim 7, wherein the lysis buffer comprises at least one detergent selected from: CHAP, CHAPS, CHAPSO, big CHAP, octylthioglucoside, and sodium deoxycholate.
11. The AAV production system of claim 1, wherein the enhancer comprises sodium propionate, caffeine, sodium butyrate, apicidin, belinostat, CI-994, CRA-024781, curcumin, panobinostat, sodium phenylbutyrate, suberoylanilide hydroxamic acid, trichostatin A, and/or valproic acid.
12. The AAV production system of claim 11, wherein the enhancer comprises sodium butyrate, sodium propionate, and/or caffeine.
13. The AAV production system of claim 1, wherein the mammalian cells are HEK293 cells or a derivative of HEK293 cells.
14. The AAV production system of claim 13, wherein the HEK293 cells are HEK293F cells or a clonal derivative of HEK293F cells.
15. The AAV production system of claim 13, wherein the HEK293 cells are cultured in suspension at a density of at least $2 \times 10^6$ cells/mL and about $2 \times 10^7$ cells/mL.
16. The AAV production system of claim 1, wherein the one or more packaging plasmids encode genes for AAV serotypes 1, 2, 3, 4, 5, 6, 7, 8, 9, DJ or DJ/8.
17. The AAV production system of claim 1, wherein helper virus components are present in the cells.
18. The AAV production system of claim 1, wherein the system is serum-free.

19. The AAV production system of claim 1, where in the system produces an AAV viral particle titer of at least about $2\times10^{10}$ viral genomes per milliliter (vg/mL) is produced.

20. The AAV production system of claim 1, wherein the system is contained in a bioreactor.

* * * * *